United States Patent
Zhou et al.

(10) Patent No.: US 9,792,404 B2
(45) Date of Patent: *Oct. 17, 2017

(54) METHOD AND SYSTEM FOR KNOWLEDGE PATTERN SEARCH AND ANALYSIS FOR SELECTING MICROORGANISMS BASED ON DESIRED METABOLIC PROPERTY OR BIOLOGICAL BEHAVIOR

(71) Applicants: Charles C Zhou, Cupertino, CA (US); Ying Zhao, Cupertino, CA (US)

(72) Inventors: Charles C Zhou, Cupertino, CA (US); Ying Zhao, Cupertino, CA (US)

(*) Notice: Subject to any disclaimer, the term of this patent is extended or adjusted under 35 U.S.C. 154(b) by 871 days.

This patent is subject to a terminal disclaimer.

(21) Appl. No.: 14/093,520

(22) Filed: Dec. 2, 2013

(65) Prior Publication Data

US 2014/0088883 A1     Mar. 27, 2014

Related U.S. Application Data

(60) Continuation-in-part of application No. 11/949,049, filed on Dec. 3, 2007, now abandoned, and a division of application No. 13/371,469, filed on Feb. 12, 2012, now Pat. No. 9,026,373.

(51) Int. Cl.
*G06F 19/10* (2011.01)
*G06F 19/24* (2011.01)
*G06F 19/18* (2011.01)
*G06F 19/12* (2011.01)

(52) U.S. Cl.
CPC .............. *G06F 19/24* (2013.01); *G06F 19/12* (2013.01); *G06F 19/18* (2013.01)

(58) Field of Classification Search
None
See application file for complete search history.

(56) References Cited

PUBLICATIONS van der Werf et al. (J. Ind. Microbiol. Biotecnol. (2005) vol. 32:234-252).*
Uchiyama (Nucleic Acids Research (2003) vol. 31:58-62).*
Markowitz et al. (Nucleic Acids Research (2006) vol. 34:D344-D348).*
Kalia et al. (Trends in Biotechnology (2003) vol. 21:152-156).*

* cited by examiner

*Primary Examiner* — Lori A Clow
(74) *Attorney, Agent, or Firm* — Invent Capture, LLC.; Samuel S. Cho

(57) ABSTRACT

Methods and systems for knowledge pattern search and analysis for selecting microorganisms based on desired metabolic properties or biological behaviors are disclosed in various embodiments of the invention. In one embodiment of the invention, a computer-implemented method for selecting a purpose-specific microorganism first compiles microorganisms' profiles by linking each microorganism's methanogenic, hydrogenic, electrogenic, another metabolic property, and/or another biological behavior to genetic and chemical fingerprints of metabolic and energy-generating biological pathways. Then, based on the compiled profiles of the microorganisms, the computer-implemented method groups the microorganisms into pathway characteristics using machine-learning and pattern recognition performed on a computer system, and subsequently generates a prediction called "discovered characteristics" for a desired metabolic property or a desired biological behavior of at least one microorganism. Furthermore, a profile match score may be calculated to indicate usefulness of one or more microorganisms for renewable energy generation from biological waste materials or wastewater.

13 Claims, 16 Drawing Sheets

| Smart Properties | How many microorganisms have the smart properties | Microorganism population size | Percentage |
|---|---|---|---|
| electrogenic | 166 | 688 | 24% |
| AD | 210 | 688 | 31% |
| methanogenic | 26 | 688 | 4% |
| hydrolytic | 94 | 688 | 14% |
| cathode | 20 | 688 | 3% |
| acidogenic | 112 | 688 | 16% |
| acetogenic | 1 | 688 | 0% |

300A

| Pathway Characteristics | Percentage of Microorganism in the Population | Methanogenic | Lift |
|---|---|---|---|
| Tetrachloroethene_degradation_High | 10.46% | 47.36% | 4.53 |
| Pyruvate/Oxoglutarate_oxidoreductases_High | 3.78% | 15.79% | 4.18 |
| ATPases_High | 3.05% | 10.50% | 3.44 |
| C5-Branched_dibasic_acid_metabolism_High | 10.61% | 26.32% | 2.48 |
| Biotin_metabolism_High | 4.51% | 5.26% | 1.17 |
| Metabolic_Efficiency_Low | 11.34% | 52.63% | 4.64 |

Knowledge pattern discovery process

900

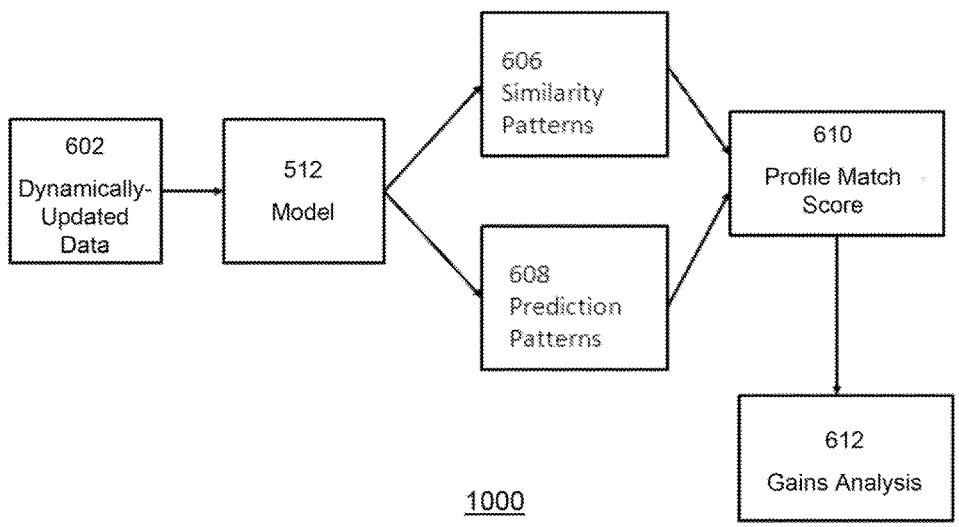

Apply knowledge patterns for detection, monitoring and prediction

EQ. 1001
$$\text{Concept Projection of } \tau = \frac{\sum All\ CC\ in\ \tau}{\sqrt{\#\ of\ unique\ context\ in\ \tau}}$$

EQ. 1003
$$\text{Gaussian distance to Cluster } l = \frac{e^{-\frac{1}{2}\|Concept\ Projection\ of\ \tau(m \times 1) - Average\ SC(m,l)\|}}{\sum_l e^{-\frac{1}{2}\|Concept\ Projection\ of\ \tau(m \times 1) - Average\ SC(m,l)\|}}$$

FIG. 10

Components in A Knowledge Visualizer

1100

Link to other agents to form a search network

1200

A collaborative search return results from a search network.

1300

Interactions and relations between parts.

1400

Table 1. Context and Element Relation (EC Matrix)

| | Context $n$ $(n=1,...K)$ |
|---|---|
| Element $W_k$ $(k=1,2,...,K)$ | EC=Association between $Wk$ and Context $n$ |

- Probability: $P(W_k|n) = \dfrac{\text{\# of instances when } W_k \text{ follows (or precedes) } n}{\text{\# of instances of } n}$
- Lift: $L(W_k, n) = \dfrac{P(W_k|n)}{P(W_k)}$
- Difference: $D(W_k, n) = P(W_k|n) - P(W_k)$
- Correlation: $R(W_k, n) = \dfrac{\sum_{t=1}^{T}(\# W_k \text{ in } t) \cdot (\# \text{ of } n \text{ in } t)}{\sqrt{\sum_{t=1}^{T}(\# \text{ of } W_k \text{ in } t)^2} \cdot \sqrt{\sum_{t=1}^{T}(\# \text{ of } n \text{ in } t)^2}}$ Table 2. Context and Concept Relation (CC matrix)

| | Context $n$ $(n=1,2,...,N)$ |
|---|---|
| Concept $m$ $(m=1,2,...,M)$ | CC=Average EC of the elements belonging to Concept $m$ |

FIG. 15

Table 3. Concept and Sequence Relation (SC Matrix)

|  | Concept m (m=1,2,...,M) |
|---|---|
| Sequence t (t=1,2,...,T) | $SC = \dfrac{\sum All\ CC\ in\ t}{\sqrt{\#\ of\ unique\ context\ in\ t}}$ |

Table 4. Concept and Cluster Relation

|  | Concept m (m=1,2,...,M) |
|---|---|
| Cluster (l=1,2,...,L) | Average SC for the sequences belong to Cluster l |

FIG. 16

Table 5. A CCC Model

| Key | Value |
|---|---|
| Context n Concept m | CC(n, m) |
| ... | ... |
| Concept m Cluster l | Average SC (m, l) |
| ... | ... |
| Num of Contexts | N |
| Num of Concepts | M |
| Num of Clusters | L |

FIG. 17

METHOD AND SYSTEM FOR KNOWLEDGE PATTERN SEARCH AND ANALYSIS FOR SELECTING MICROORGANISMS BASED ON DESIRED METABOLIC PROPERTY OR BIOLOGICAL BEHAVIOR

BACKGROUND OF THE INVENTION

The present invention relates generally to metabolic reaction networks of microorganisms. More specifically, the present invention relates to identifying, discovering, and customizing microorganisms for generating environmentally-friendly energy from biological waste materials by utilization of certain desired metabolic properties or desired biological behaviors.

Historically, human civilizations have flourished around abundant water supplies. Successful continuity of cities is often contingent upon easy accessibility to water. Water is one of the most vitally necessary yet frequently overlooked resources for human survival. Due to an ever-increasing level of human impacts on the environment in modern civilization, water pollution has become an increasingly significant problem. The wastewater generated by anthropogenic influences need to be processed daily to ensure clean water consumption and environmental protection.

Several methods of conventional and biological treatments of wastewater have been widely used in the wastewater treatment industry, some of which include trickling bio-filter, activated sludge process, and suspended growth treatment systems. Currently, industrial wastewater is typically treated by aerobic systems that remove contaminants prior to discharging the water to river, lake or underground. Although the aerobic system is effective at cleaning waters, a major drawback is that these treatment systems require large amounts of electricity for proper operation. For example, annual power usage of a single residential aerobic wastewater treatment system is in the range of 750 to 1500 kWh. Aerobic systems also require continuous air supply which adds substantial maintenance cost for long term operation. The current wastewater treatment plants in the U.S. are estimated to consume approximately 5% of national electricity to perform wastewater treatment, which is equivalent to about $10 billion dollars. Another disadvantage of the aerobic wastewater treatment system is the production of large amounts of sludge. In a conventional aerobic wastewater treatment process, after aeration by the aerobic bacteria, sludge is generated in the form of wastewater residues, which require additional processing. Typically, this sludge is transported to landfills to decompose, which raises additional environmental pollution concerns. Furthermore, the aerobic process reduces the dissolved oxygen in the wastewater which is detrimental to fish and other aquatic life.

Another method of wastewater treatment involves using anaerobic systems that do not require free oxygen from the treatment process. The anaerobic systems generally require less electricity and are particularly useful for treatment of wastewater which has a high concentration of biodegradable organic materials (i.e. a high level of microorganisms such as bacteria, fungi, archaea, and protists). For example, in the food processing industry or small-scale wastewater treatment facilities, the annual power usage of a single anaerobic wastewater treatment system is in the range of 50~100 kWh, which is approximately 7% of a comparable aerobic wastewater treatment system. Some anaerobic wastewater treatment systems can be further utilized to produce methane via anaerobic digestion by microorganisms. Furthermore, at least in a laboratory environment, electricity can be directly produced using the microbial fuel cell (MFC) technology involving anaerobic respiration of microorganisms. For the environmentally-friendly utilization of recycled energy, the generated methane from an anaerobic wastewater treatment system may be used to operate a methane-powered electrical plant, or be used as bottled sources of energy (e.g. heating fuels, and etc.). Similarly, the generated electricity from the MFC's can be utilized as a source of electrical energy.

However, typical wastewater used as feeds in an anaerobic wastewater treatment system are too dilute to be an efficient methane generator, resulting in a low methane-generating (i.e. methanogenic) efficiency. Similarly, although MFC's can generate electrical currents by using electrogenic bacteria as catalysts in an anaerobic wastewater treatment system or another type of wastewater treatment system, the efficiency of electricity generation (i.e. electrogenic efficiency) is substantially less than desirable, because microorganisms present in the wastewater are not optimized for electrogenic efficiency.

Therefore, a novel method and a related system for knowledge pattern search and analysis for identifying and selecting particularly useful microorganisms for a desired metabolic property or a desired biological behavior (e.g. a high methanogenic efficiency, a high electrogenic efficiency, and etc.) may be highly beneficial in improving efficiency of environmentally-friendly energy generation from biological waste materials.

Furthermore, utilizing a novel method of knowledge pattern search and analysis which can discover useful information patterns and meaningful information from an existing library of genetic and genome database and/or an empirical sample of wastewater or other biological waste materials may be highly beneficial for convenient and continued identification of particularly useful microorganisms for a desired metabolic property or a desired biological behavior.

In addition, discovering meaningful information patterns and usefulness of one or more microorganisms by utilizing semantical analysis and collaborative search returns of various pieces of disjointed yet new and unique information from multiple biochemical and genetic information sources by utilizing multiple learning agents may also be highly beneficial for users who are dynamically and continuously searching for useful microorganisms with a particular metabolic property or a biological behavior.

SUMMARY

Summary and Abstract summarize some aspects of the present invention. Simplifications or omissions may have been made to avoid obscuring the purpose of the Summary or the Abstract. These simplifications or omissions are not intended to limit the scope of the present invention.

In one embodiment of the invention, a method for selecting microorganisms to generate environmentally-friendly energy from biological waste materials is disclosed. This method comprises the steps of: compiling one or more microorganisms' profiles in a computer database system by linking each microorganism's methanogenic, hydrogenic, electrogenic, acidogenic, acetogenic, hydrolytic, another metabolic property, or another biological behavior to genetic and chemical fingerprints of metabolic and energy-generating biological pathways; grouping one or more microorganisms into pathway characteristics by using machine-learning and pattern recognition performed on a CPU and a memory unit of a computer system, wherein computer system takes the one or more microorganisms' profiles from the computer database system as inputs for machine-learning and pattern-recognition-based analysis; generating discovered characteristics and profile match scores among at least a subset of the one or more microorganisms based on the machine-learning and pattern recognition performed on the CPU and the memory unit of the computer system, wherein each discovered characteristics represents a prediction for a desired metabolic property or a desired biological behavior of at least one microorganism; and selecting one or a group of microorganisms based on the profile match scores generated from the computer system with the CPU and the memory unit, wherein a higher profile match score represents a higher usefulness of the one or the group of microorganisms with one or more desired discovered characteristics for generating the environmentally-friendly energy from the biological waste materials.

In another embodiment of the invention, a method for selecting microorganisms to generate methane, hydrogen, and/or electricity from biological waste materials is disclosed. This method comprises the steps of: compiling one or more microorganisms' profiles in a computer database system by linking each microorganism's ability to generate methane, hydrogen, and/or electricity to genetic and chemical fingerprints of metabolic and energy-generating biological pathways, wherein each microorganism's ability to generate methane, hydrogen, and/or electricity can be nurtured by an anaerobic fermentation that accommodates biochemical interactions or digestion of the biological waste materials by at least a subset of the microorganisms; grouping one or more microorganisms into pathway characteristics by using machine-learning and pattern recognition performed on a CPU and a memory unit of a computer system, wherein computer system takes the one or more microorganisms' profiles from the computer database system as inputs for machine-learning and pattern-recognition-based analysis; generating discovered characteristics and profile match scores among at least a subset of the one or more microorganisms based on the machine-learning and pattern recognition performed on the CPU and the memory unit of the computer system, wherein each discovered characteristics represents a prediction of at least one microorganism's ability to generate methane, hydrogen, and/or electricity; and selecting one or a group of microorganisms based on the profile match scores generated from the computer system with the CPU and the memory unit, wherein a higher profile match score represents a higher usefulness of the one or the group of microorganisms for generating methane, hydrogen, and/or electricity from the biological waste materials.

BRIEF DESCRIPTION OF DRAWINGS

FIG. 3 shows a first table, which contains useful metabolic properties (i.e. also referred herein as "smart properties") of microorganisms, and a second table, which contains exemplary categories of "pathway characteristics" and associated quantitative measures, in accordance with an embodiment of the invention.

FIG. 10 shows an exemplary method of applying a constructed pattern-identifying model to static and dynamically-updated data associated with a computerized data network for data pattern analysis, calculation of a data profile match score, and/or a gains analysis, in accordance with an embodiment of the invention.

FIG. 15 shows Table 1 and Table 2. Table 1 shows a method of an EC matrix (element-and-context relation), which may be quantified with a "probability" calculation, a "lift" calculation, a "difference" calculation, and a "correlation" calculation, in accordance with an embodiment of the invention.

Figure 1:
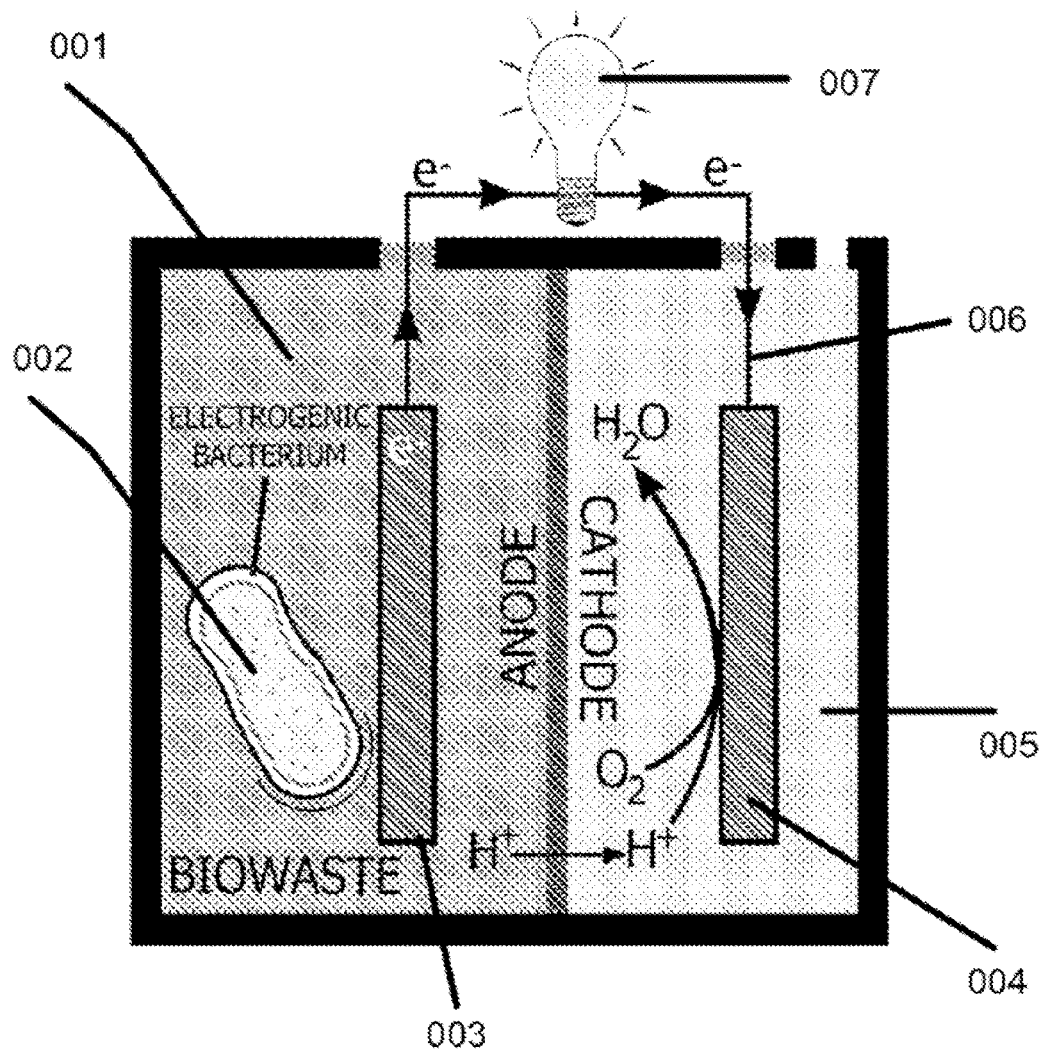
FIG. 1 shows an example of an microbial fuel cell (MFC) in accordance with an embodiment of the invention.

Table 2 shows a method of a CC matrix (context-and-concept relation), in accordance with an embodiment of the invention.

FIG. 16 shows Table 3 and Table 4. Table 3 shows a method of a SC matrix (concept-and-sequence relation), in accordance with an embodiment of the invention.

Table 4 shows an example of a concept-and-cluster relation, in accordance with an embodiment of the invention.

FIG. 17 shows Table 5, which illustrates a context-concept-cluster (CCC) matrix, in accordance with an embodiment of the invention.

DETAILED DESCRIPTION

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

The detailed description is presented largely in terms of description of shapes, configurations, and/or other symbolic representations that directly or indirectly resemble one or more methods and systems for knowledge pattern search and analysis for selecting microorganisms based on desired metabolic property or biological behavior. These descriptions and representations are the means used by those experienced or skilled in the art to most effectively convey the substance of their work to others skilled in the art.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment. Furthermore, separate or alternative embodiments are not necessarily mutually exclusive of other embodiments. Moreover, the order of blocks in process flowcharts or diagrams representing one or more embodiments of the invention do not inherently indicate any particular order nor imply any limitations in the invention.

For the purpose of describing the invention, a term "metabolic property" is defined as a biochemical trait of a microorganism. For example, a microorganism that can generate electricity is "electrogenic." In another example, a microorganism that can generate hydrogen is "hydrogenic." Yet in another example, a microorganism that can generate methane is "methanogenic." Yet in another example, a microorganism that can generate acids is "acidogenic." Yet in another example, a microorganism that can generate aceta is "acetogenic." Yet in another example, a microorganism that can separate water molecules into hydrogen ions ($H+$, also referred as protons) and hydroxy ions ($OH-$) is "hydrolytic."

Furthermore, for the purpose of describing the invention, a term "biological behavior" is defined as one or more observable capabilities of microorganisms, such as the capabilities to produce electricity, hydrogen, and methane, which are related to underlying biological or chemical interaction of a microorganism with chemicals or other microorganisms. In some embodiments of the invention, the term "biological behavior" may be interchangeably used with the term "metabolic property."

In addition, for the purpose of describing the invention, a term "pathway" is defined as a number of biochemical steps or links, with a start and an end. Some typical types of biochemical pathways are metabolic pathways, which involve a series of biochemical reactions occurring within a cell in a flow of molecules such as one or more of enzymes, substrates, and/or products associated with one or more microorganisms.

Moreover, for the purpose of describing the invention, a term "pathway characteristics" is defined as a collection of biochemical reactions involving one or more of enzymes, substrates, and/or products.

Furthermore, for the purpose of describing the invention, a term "discovered characteristics" is defined as a prediction for a desired metabolic property or a desired biological behavior of at least one microorganism.

In addition, for the purpose of describing the invention, a term "anaerobic digestion" is defined as a process in which organic matters are broken down primarily into methane and carbon dioxide by anaerobic bacteria under anaerobic conditions.

Moreover, for the purpose of describing the invention, a term "microorganism's profile" is defined as texts or other data which describe genomic information, codon usages, gene distributions along a metabolic and energy-generating biological pathway, gene distributions for a particular functional category, gene similarity among one or more microorganisms, and/or generic functions of genes.

Furthermore, for the purpose of describing the invention, a term "profile match score" is defined as a quantitative measure which represents usefulness of one or more microorganisms with desired discovered characteristics for generating environmentally-friendly energy from biological waste materials. For example, a higher profile match score indicates a higher level of usefulness for one or more microorganisms, while a lower profile match score indicates a lower level of usefulness for one or more microorganisms for generation of environmentally-friendly energy form biological waste materials.

In addition, for the purpose of describing the invention, a term "element" is defined as a piece of information associated with one or more microorganisms' profiles, and a term "sequence" is defined as a set of ordered elements.

Moreover, for the purpose of describing the invention, a term "contextualization" is defined as using a user-defined context (e.g. a condition, a keyword, an element, or a desired target information) to identify certain information which contains these contexts. For example, if the user-defined context is finding information regarding highest gene similarity scores, gene usages in metabolic pathways (e.g. enzymes, substrates, and/or products), or percentage of gene usages in certain functional categories in Kyoto Encyclopedia of Genes and Genomes (KEGG) or another library of genetic and/or genome data, then pertinent information may be identified by a system for the knowledge pattern search in accordance with an embodiment of the present invention. This process of finding information based on the user-defined context is called "contextualization."

Furthermore, for the purpose of describing the invention, a term "conceptualization" is defined as grouping information (e.g. elements) together based on an EC (element-and-context) matrix and a CC (context-and-concept) matrix. In one embodiment of the invention, conceptualization may be particularly useful if certain information falls outside of the user-defined context and needs to be grouped with other elements and contexts. For example, if a first set of gene or genome information for a first microorganism is within the user-defined context, but a second set of gene or genome information for a second microorganism is outside of the user-defined context, then a process of conceptualization may involve discovering which data are most closely associated with other elements and contexts (e.g. pathway characteristics) for a subsequent generation of discovered characteristics. In a preferred embodiment of the invention, the EC matrix and CC matrix calculation approach enables the system for the knowledge pattern search to group unfamiliar (e.g. outside the range of user-defined context) information together with other information which are determined to be closely associated with this unfamiliar information, thus to reveal the meaning and significance of the unfamiliar information, which may be "discovered characteristics," or a prediction for a desired metabolic property or a desired biological behavior of at least one microorganism. In the preferred embodiment of the invention, the process of associating an unfamiliar piece of information with other information based on element-and-context (EC) and context-and-concept (CC) relational calculations is called "conceptualization."

In addition, the purpose of describing the invention, a term "clustering" is defined as grouping and storing information into a plurality of clusters, each of which is based on proximity or "closeness" of information determined by contextualization and conceptualization processes. For example, a list of elements may be produced as an output of contextualization, and a list of concepts may be produced as an output of conceptualization. In this example, if the list of elements (e.g. pieces of information associated with one or more microorganisms' profiles) and the list of concepts (e.g. discovered characteristics) have similar pathway characteristics (i.e. collection of reactions) based on a probability calculation, a lift calculation, a difference calculation, a correlation calculation, an EC matrix, a CC matrix, and/or a standard deviation among elements, contexts, concepts, and sequences, then this list of elements and the list of concepts may be categorized and stored in the same cluster.

In addition, for the purpose of describing the invention, a term "generic learning procedure" is defined as an intelligent procedure capable of deriving one or more rules (i.e. discovered characteristics) from conditions, patterns, data collection, historical data, and other sources of information. In a preferred embodiment of the invention, a generic learning procedure may be used in a learning agent, a mining engine, and/or a normal data profile construction for data analysis and rule creations.

Furthermore, for the purpose of describing the invention, a term "agent" is defined as a data collection or a monitoring mechanism in a domain. In a preferred embodiment of the invention, a learning agent may be configured to collect, consider, and/or incorporate more than one source or one dimension of information. For example, a learning agent can develop a simple or complicated rule based on a generic learning procedure from historical or collected data.

One aspect of an embodiment of the present invention is disclosing a computerized system for knowledge pattern search and analysis for selecting microorganisms based on a desired metabolic property or a desired biological behavior.

Another aspect of an embodiment of the present invention is disclosing a method for knowledge pattern search, analysis, discovery characteristics generation, and profile match score generation for selecting microorganisms based on a desired metabolic property or a desired biological behavior, wherein the method utilizes a computerized system.

In one embodiment of the invention, this computerized system can conduct a context-concept-cluster (CCC) data analysis on historical data to construct a pattern-identifying model, which can then be used to identify patterns, discovery characteristics, and profile matches from static and dynamically-updated data sources. Based on the pattern-identifying model comparison against static and dynamically-updated data, this computerized system may also generate profile match score and gains analysis results for the static and dynamically-updated data.

Another aspect of an embodiment of the present invention is disclosing a method for knowledge pattern search and analysis from a plurality of networked agents which have access to genetic, genome, and/or biochemical databases for microorganisms, wherein the method utilizes a computerized system for its procedures.

Most anaerobic wastewater or biological waste material treatment systems operate in absence of external source of oxygen during the treatment process. Anaerobic digestion provided by microorganisms within wastewater and/or biological waste materials enable an anaerobic respiration process, which may produce hydrogen, methane, electricity, and other forms of recycled energy for potential energy utilization. A great advantage of an anaerobic wastewater treatment system is its ability to generate environmentally-friendly energy with minimal energy consumption during the wastewater treatment process. By using anaerobic microorganisms and their inherent fermentation pathways, hydrogen, methane, electricity, or other forms of energy can be directly harvested during or after the wastewater treatment process.

However, identifying and selecting useful or "smart" microorganisms for boosting efficiency of the energy generation from biological waste materials may be critical in practical operation of anaerobic wastewater treatment systems for an environmentally-friendly energy generation, because methanogenic, hydrogenic, and/or electrogenic microorganisms are not sufficiently present in typical wastewater or biological waste materials to produce an acceptable level of electricity, hydrogen, or methane relative to the cost of operation.

For example, although methane production via anaerobic digestion is a mature process that has been most commonly used within full-scale wastewater facilities in recent years, it has shown some significant operational inefficiencies. In case of methane generation, wastewater in an anaerobic wastewater treatment system is too dilute to produce methane efficiently. Identifying, selecting, and over-expressing certain methanogenic microorganisms in the wastewater may be important for boosting the efficiency of methane generation. Similarly, although the microbial fuel cell (MFC) technology enables electrical generation from dissolved biomass, most MFC's are not sufficiently efficient to be used for electrical generation in a commercial scale, in part because of a lack of density of efficient electrogenic microorganisms in wastewater composition. Therefore, in order to provide an efficient level of electrical generation from the MFC's, it may also be important to identify, select, and over-express (i.e. over-populate) electrogenic microorganisms in wastewater composition for efficient operation of the MFC's.

FIG. 1 shows an example of an microbial fuel cell (MFC) (100) in accordance with an embodiment of the invention. In a preferred embodiment of the invention, electrogenic microorganism (002) in an anodic compartment (001) is configured to cause oxidative conversions of organic substances, while in a cathodic compartment (005), chemical and microbial reductive processes can occur. The anodic compartment (001) contains wastewater and/or biological waste materials, while an anode (003) in the anodic compartment (001) is electrically connected to a cathode (004) in the cathodic compartment (005) via an electrical wire (006). In the preferred embodiment of the invention, an external appliance (007) may also be operatively connected to the anode (003) and the cathode (004).

As illustrated by FIG. 1, MFC's are devices that generate current by using bacteria as the catalysts to oxidize organic or inorganic substances. In one embodiment of the invention, electrons produced by the bacteria from these substrates can be transferred to the anode (003, negative terminal), and then flow to the cathode (004, positive terminal) through a conductive material such as an electrical wire (006). There are several ways to transfer electrons to the anode, such as electron mediators or shuttles, direct membrane associated electron transfer, nanowires produced by the bacteria, and etc. If no exogenous mediators are added to the system, this type of MFC may be classified as a "mediator-less" MFC.

In one embodiment of the invention, anaerobically-respiratory bacteria may be utilized for production of electrons. MFC's may operate using these bacteria either through pure cultures or mixed cultures. Bacteria such as *Shewanella putrefaciens, Pseudomonas aeruginosa, Geobacter* sp., *Rhodoferax ferrireducens* may be used in pure culture-operated MFC's from several studies. Thermophilic bacteria, such as *Bacillus licheniformis* or *Bacillus thermoglucosidasius* may also be used for MFC's operating at high temperature. In mixed culture-operated MFC's, each MFC's performance is determined by the interaction of the whole microbial community, namely "electrochemically active consortium." The sources of the mixed cultures are either from sediments (e.g. marine and lake sediments) or activated sludge from wastewater treatment plants.

In one embodiment of the invention, the "electrochemically active consortia" for a mixed culture-operated MFC may include *Geobacter* sp., *Desulfuromonas* sp., *Alcaligenes faecalis, Enterococcus faecium, Pseudomonas aeruginosa, Clostridium* sp., *Bacteroides* sp., *Aeromonas* sp., and *Brevibacillus* sp. Mixed culture-operated MFC's are generally capable of producing more electrical power than comparable pure culture-operated MFC's, presumably due to a higher resistance against process disturbances, a greater substrate versatility, and a higher power output in the mixed culture-operated MFC's than in the pure culture-operated MFC's.

For efficient generation of electricity from MFC's, it is imperative that electrogenically-efficient bacteria or other microorganisms are prevalent in wastewater or biological waste materials. Therefore, identification and selection of efficient microorganisms for certain metabolic properties or biological behaviors (e.g. methanogenic, hydrogenic, and/or electrogenic efficiencies) can play a key role in improving efficiency and energy generation capacity from wastewater or biological waste material treatment facilities.

The present invention discloses a knowledge pattern learning and search method and a related computerized system for selecting microorganisms to generate environmentally-friendly energy from wastewater or biological waste materials. In a preferred embodiment of the invention, an in silico knowledge pattern search and analysis method for selecting microorganisms based on a desired metabolic property or a desired biological behavior involves multiple steps.

In the preferred embodiment of the invention, the first step is compiling microorganisms' profiles by linking massive amount of genetic and chemical fingerprints in the metabolic and energy-generating biological pathways (e.g. codon usages, gene distributions in function categories, etc.) to the microorganisms' biological behaviors or metabolic properties. Then, the second step involves a machine learning and pattern recognition system, which can be used to group one or more microorganisms into pathway characteristics based on the microorganisms' profiles.

A subsequent step involves generating discovered characteristics and profile match scores among at least a subset of microorganisms based on the machine-learning and pattern recognition (i.e. knowledge pattern search and analysis) performed on a CPU and a memory unit of the computer system. In one embodiment of the invention, the discovered characteristics typically represent a prediction for a desired metabolic property or a desired biological behavior of at least one microorganism. Then, one or a group of microorganisms may be identified and selected based on profile match scores generated from the computer system, wherein a higher profile match score represents a higher usefulness of the one or the group of microorganisms with one or more desired discovered characteristics for generating environmentally-friendly energy from biological waste materials or wastewater.

In one embodiment of the invention, microorganisms' metabolic capabilities to digest a required organic matter and generate environmentally-friendly energy from treating organic wastewaters are evaluated using a knowledge pattern search and analysis method, as described in various figures and associated descriptions for the present invention. By selecting most effective microorganisms for both waste reduction and renewable energy generation based on the content of biological waste materials available for a particular sewage treatment facility, cleaning and renewable energy generation efficiency can be significantly improved.

For example, in one embodiment of the invention, as a product of renewable energy, hydrogen can be recovered from an anaerobic fermentation process accompanying the wastewater treatment, and the end products from the fermentation process can be fed into a Microbial Fuel Cell (MFC) process to generate electricity as a product of renewable energy and at the same time treat the wastewater. Various embodiments of the present invention can be used to identify and select the most useful microorganisms for efficiently generating hydrogen, electricity, methane, or other desired forms of renewable energy by analyzing metabolic properties and biological behaviors of microorganisms using knowledge pattern search and analysis methods on genetic and genome databases and/or samples of specific waste materials.

In a preferred embodiment of the invention, a method and a related system for knowledge pattern search and analysis for selecting microorganisms based on desired metabolic properties or biological behaviors provide an efficient and sustainable method to generate environmentally-friendly energy, which may offset the treatment costs associated with biological waste materials. One or more embodiments of the invention may also reduce experimental costs associated with microorganism selections for renewable energy utilization, because the knowledge pattern search and analysis used in the present invention can reduce trial-and-error costs and effort for identification and selection of microorganisms even before any experiments with sewage or biological waste material samples.

In general, various embodiments of the present invention utilizes an in silico (i.e. performed on a computer or a computerized simulation) knowledge pattern search and analysis method and system called "Computer-Assisted Strain Construction and Development Engineering," or "CASCADE." CASCADE is developed in part under a SBIR Phase II contract from the US Army, and is also an extension of an earlier system QIS $D^2$ (Quantum Intelligence System for Drug Discovery) developed in part from DARPA SBIR Phase II Award (May 2004-May 2006), titled "Development of Predictive Algorithms for In Silico Drug Toxicity and Efficacy Assessment."

CASCADE is associated with developing predictive algorithms for accurately predicting drug toxicity and efficacy from multiple data sources. A QIS $D^2$ model is designed to be successfully trained, tested and validated on evidence data sets (e.g. experimental, logical, and etc.) for predicting the potential in vitro or in vivo effects of drug molecules in biological systems. Of particular interest are the effects arising from chemical and biological agents and pathogens. QIS $D^2$ system is designed to model the data from various sources, including data and text, and integrating them for biochemical characteristics discovery, using knowledge pattern search and analysis as described in, for example, FIGS. 2, 4, 5, 9-14, and associated descriptions in the specification. Sensitivity analysis for biochemical targets of interest can also be performed using the QIS $D^2$ system, and accurately predict biochemical targets of interest using a large number of attributes.

With CASCADE and QIS $D^2$ system and method, a user is able to predict thousands of biochemical targets and their characteristics simultaneously and conveniently. In various embodiments of the invention, at least some aspects of QIS $D^2$ methodology has been applied in CASCADE development to link massive genetic and chemical fingerprints in the metabolic and energy-generating biological pathways to assess a microorganism's metabolic capability to digest the organic matters and generate renewable energy. Furthermore, in various embodiments of the present invention, the CASCADE method and system are applied for selection and identification of useful microorganisms with desirable metabolic properties or biological behaviors for wastewater and biological waste materials treatment processes.

Figure 2:
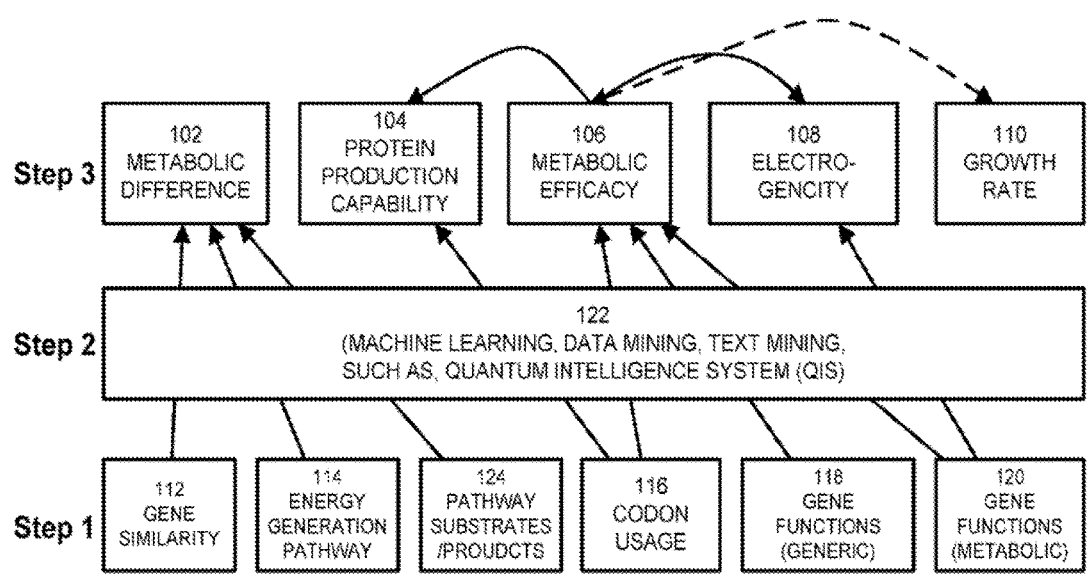
FIG. 2 shows high-level in silico processes for using knowledge pattern search and learning for identification and selection of desired microorganisms, in accordance with an embodiment of the invention.

FIG. 2 shows high-level in silico processes (200) for using knowledge pattern search and learning for identification and selection of desired microorganisms, in accordance with an embodiment of the invention. In a preferred embodiment of the invention, the following steps are substantive and novel procedures for identifying and selecting microorganisms based on a unique method of knowledge pattern search and learning (122), which are also described in associated with other figures in the specification.

As shown in FIG. 2, in Step 1 of the preferred embodiment of the invention, a profile of a microorganism is compiled using a variety of genetic, genome, and biochemical information resources, such as existing databases, libraries, and/or dynamic samples of biochemical specimen (e.g. from wastewater or biological waste material samples in a sewage treatment facility). For a particular microorganism and a particular content of biological waste material input (e.g. pathway substrate/products (124)), and a desired environmentally-friendly energy output (e.g. 206, 210 of FIG. 6), a computer system compiles a profile for that microorganism, which are texts or other forms of data that describe the microorganism with respect to the biological waste material input, the desired environmentally-friendly energy output, and other biochemical "pathway" characteristics. For example, the microorganism's profile may describe gene similarity (112), energy generation pathway (114), codon usage (116), generic gene functions (118), metabolic gene functions (120), and pathway substrates/products (124). In one embodiment of the invention, Kyoto Encyclopedia of Genes and Genomes (KEGG) or another library of genetic and/or genome data are used in association with samples of biochemical specimen from wastewater or biological waste materials in a sewage treatment facility, wherein any pertinent genetic and biochemical information are extracted from the samples of biochemical specimen. In another embodiment of the invention, biochemical information from other sources or direct reconstruction of genomic sequences from certain microorganisms may be used during the compilation process for one or more microorganisms' profiles.

Continuing with FIG. 2, in Step 2 of the preferred embodiment of the invention, a knowledge pattern search and learning computer system (122) can group the microorganism population into pathway characteristics (e.g. 300B in FIG. 3) by applying a machine learning, data mining, text mining and pattern recognition methods (i.e. as described in FIGS. 9-14 and related descriptions, for example). This step enables grouping of the microorganism population into pathway characteristic groups using the microorganisms' profiles compiled in Step 1.

Then, in Step 3 of the preferred embodiment of the invention, discovered characteristics, which represent a prediction for a desired metabolic property or a desired biological behavior of at least one microorganism, can be generated. Examples of discovered characteristics include, but are not limited to, metabolic difference (102), protein production capability (104), metabolic efficacy (106), electrogenic properties (108), and growth rate (110) for one or more microorganisms. In one embodiment of the invention, a metabolic efficiency measure, such as average metabolic efficiency (AME), can be used to quantitatively compare one or more microorganisms' profiles and derive a profile match score. In one embodiment of the invention, a profile match score represents the usefulness of a particular microorganism or a group of microorganisms for a purpose-specific usage, such as renewable energy generation efficiencies (e.g. methanogenic, hydrogenic, and/or electrogenic efficiencies, and etc.).

Furthermore, in one embodiment of the invention, a metabolic efficiency measure may represent a prediction of a desired capability in real life based on an microorganism's profile. For example, a metabolic efficiency measure may reflect the need of a quantitative comparison metric for a particular application, as shown below:

Average number of genes in metabolic pathways (i.e. 106, 110)

Unique number of genes in metabolic pathways (i.e. 106)

Percentage of gene usages in gene function categories (i.e. 104, 108)

Average codon usage frequencies with respect to a pathway product (i.e. 104, 106)

Gene similarity (112) and difference (102) along the metabolic pathways with respect to a reference microorganism Number of substrates consumed and products produced in the reactions involved in a fermentation process (e.g. 214 of FIG. 6) which uses biological waste material input (e.g. 202 of FIG. 6) as the feeding pathway substrates (124). The desired products will be hydrogen (e.g. 206 of FIG. 6) and fermentation end products (e.g. 204 of FIG. 6), which then serve as the input substrates for the subsequent step (e.g. 208 of FIG. 6).

Figure 6:
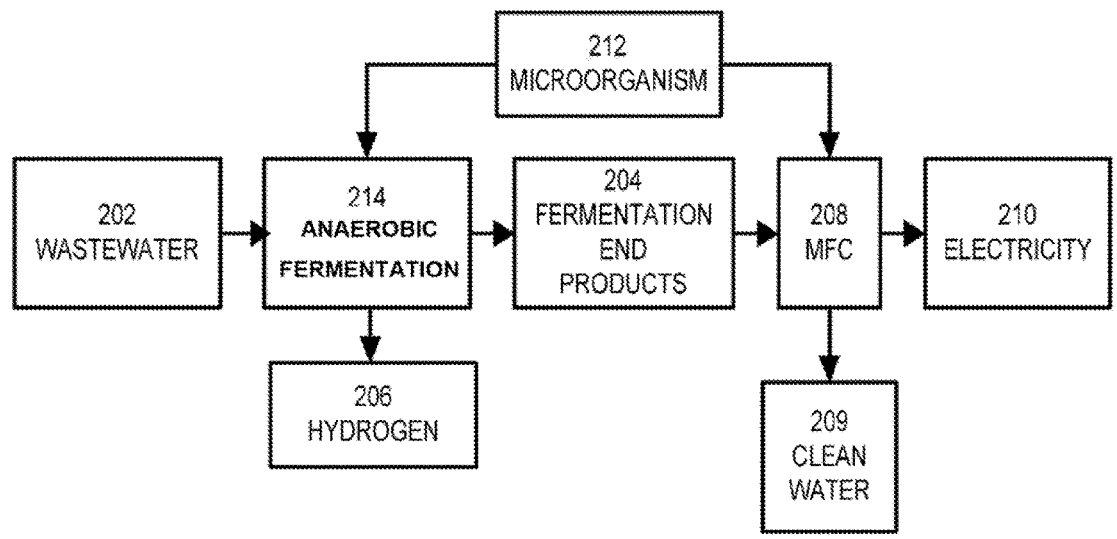
FIG. 6 shows an example of wastewater processing and environmentally-friendly energy generation from biological waste materials, in accordance with an embodiment of the invention.

Number of substrates consumed and products produced in reactions, which use the fermentation end products (e.g. 204 of FIG. 6) mentioned above as the feeding substrates (124), involving in generating the desired environmentally-friendly energy output (e.g. 208, 210 of FIG. 6).

FIG. 3 shows a first table (300A), which contains useful metabolic properties (i.e. also referred herein as "smart properties") of microorganisms in accordance with an embodiment of the invention. As shown by the sample data of metabolic properties in the first table (300A), only a minority number of microorganisms exhibits desirable metabolic properties for renewable energy generation (e.g. methanogenic, hydrogenic, electrogenic, and etc.). For example, electrogenic microorganisms are found in only 24 percent of a sample population of microorganisms in this particular table (300A), while methanogenic microorganisms are found in only 4 percent of the same sample population. Therefore, identifying and choosing microorganisms with purpose-specific metabolic properties and/or biological behaviors to enable over-expression of these chosen microorganisms in real-life loads of wastewater or biological waste materials may be critical for efficiency improvement of renewable energy generation.

FIG. 3 also shows a second table (300B) in accordance with an embodiment of the invention. The second table (300B) contains exemplary categories of "pathway characteristics" and associated quantitative measures, such as the percentage of microorganisms with particular characteristics (e.g. tetrachloroethene degradation high, pyruvate/oxoglutarate oxidoreductases high, ATPases high, and etc.) in the whole population of waste materials, the percentage of methanogenic microorganisms with particular pathway characteristics, and statistical lift values.

When a sample of a generic population of bacteria is compared against "smart" bacteria with desirable properties (i.e. a population of "methanogenic" bacteria"), a lift value can represent a ratio between smart bacteria in the smart bacteria population with a specific path characteristics vs. the generic bacteria in the generic population with the same specific path characteristics. For example, in the second table (300B) of FIG. 3, 11.34% of generic bacteria in the generic population have the characteristic "metabolic efficiency low," while 52.63% of smart bacteria with the desirable methanogenic properties in the smart bacteria population have the same characteristics, thereby resulting in a lift value of 4.64 (i.e. 52.63/11.34).

As described previously, the term "pathway characteristics" is defined as a collection of biochemical reactions involving one or more of enzymes, substrates, and/or products. In this particular example in the second table (300B) of FIG. 3, the pathway characteristics categories are a result of grouping one or more microorganisms in a sample population based on profile compilation of microorganisms. By further analyzing these pathway characteristics using a knowledge pattern search and analysis method, a computerized system can generate one or more predictions, known as "discovered characteristics," for a desired metabolic property or a desired biological behavior of at least one microorganism for efficient renewable energy generation from biological waste materials.

Figure 4:
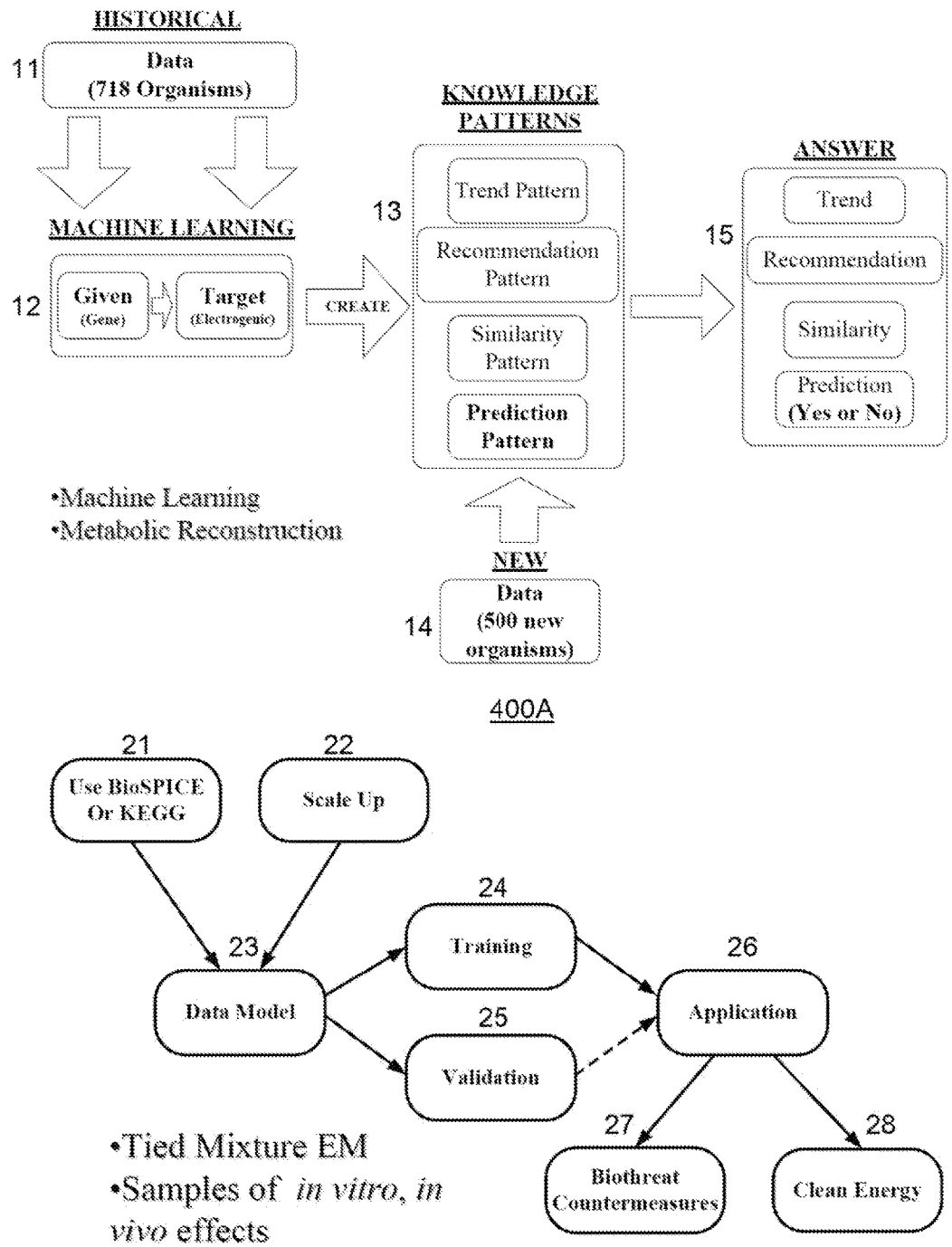
FIG. 4 shows an overall process for computer-assisted strain construction & development engineering (CASCADE) and its particular biological application, which may be used for knowledge pattern search and learning for identification and selection of desired microorganisms, in accordance with an embodiment of the invention.

FIG. 4 shows an overall process (400A) for computer-assisted strain construction & development engineering (CASCADE) and its particular biological application (400B), which may be used for knowledge pattern search and learning for identification and selection of desired microorganisms, in accordance with an embodiment of the invention. In this particular embodiment of the invention, historical data (11) such as Kyoto Encyclopedia of Genes and Genomes (KEGG) or another library of genetic and/or genome data are fed into a machine-learning computer system (12), which is configured to link microorganisms' methanogenic, hydrogenic, electrogenic, another metabolic property, or another biological behavior to genetic and chemical fingerprints of metabolic and energy-generating biological pathways (e.g. enzymes, substrate, product, and etc.) for derivation of microorganisms' profiles.

Then, as shown in FIG. 4 for the "Knowledge Patterns" block (13), knowledge pattern search and analysis can be conducted on the microorganisms' profiles and any other pertinent data (e.g. 500 new organisms (14)) using a variety of pattern analysis (e.g. trend pattern, recommendation pattern, similarity pattern, prediction pattern) to formulate and analyze pathway characteristics, which result in derivation of discovered characteristics. Discovered characteristics, which may be indication of trends, recommendations, similarities, and/or predictions among microorganisms and pathway characteristics, are derived from the "Knowledge Patterns" block and can be stored in the "Answer" block (15) in FIG. 4.

Continuing with FIG. 4, once the data modeling and "smart" microorganism identification and selection are completed using the knowledge pattern search and analysis, the selected smart microorganisms can be scaled up for a trial run with sample waste materials, or an operational run with incoming waste materials (i.e. also known as "influent"), once the trial run validates efficacy of the smart microorganisms for generation of renewable energy. In some cases, the data modeling and "smart" microorganism identification and selection approach may also be used for bio-threat countermeasures or biological material screening services.

As shown in the particular application (400B) of the computer-assisted strain construction & development engineering (CASCADE), biological data from BioSPICE or KEGG (21) can be combined with scale-up methods (22) for a trial run or a commercialization process as inputs into a computerized data model (23), which may involve machine learning (12) and knowledge pattern search (13) to find desirable trends, recommendations, similarities, and/or predictions (15) previously shown and described for the overall process (400A) for CASCADE.

Then, in one embodiment of the invention, the outputs from the computerized data model (23), which may be desirable trends, recommendations, similarities, and/or predictions, can be used for training (24) for commercialization or other activities, and/or validation (25) of hypothesis or existing data models. These results can be used in a variety of applications (26) as desired, such as clean energy development (28) and biological-threat countermeasure development (27), as shown in the particular application (400B) of the computer-assisted strain construction & development engineering (CASCADE) in FIG. 4.

Figure 5:
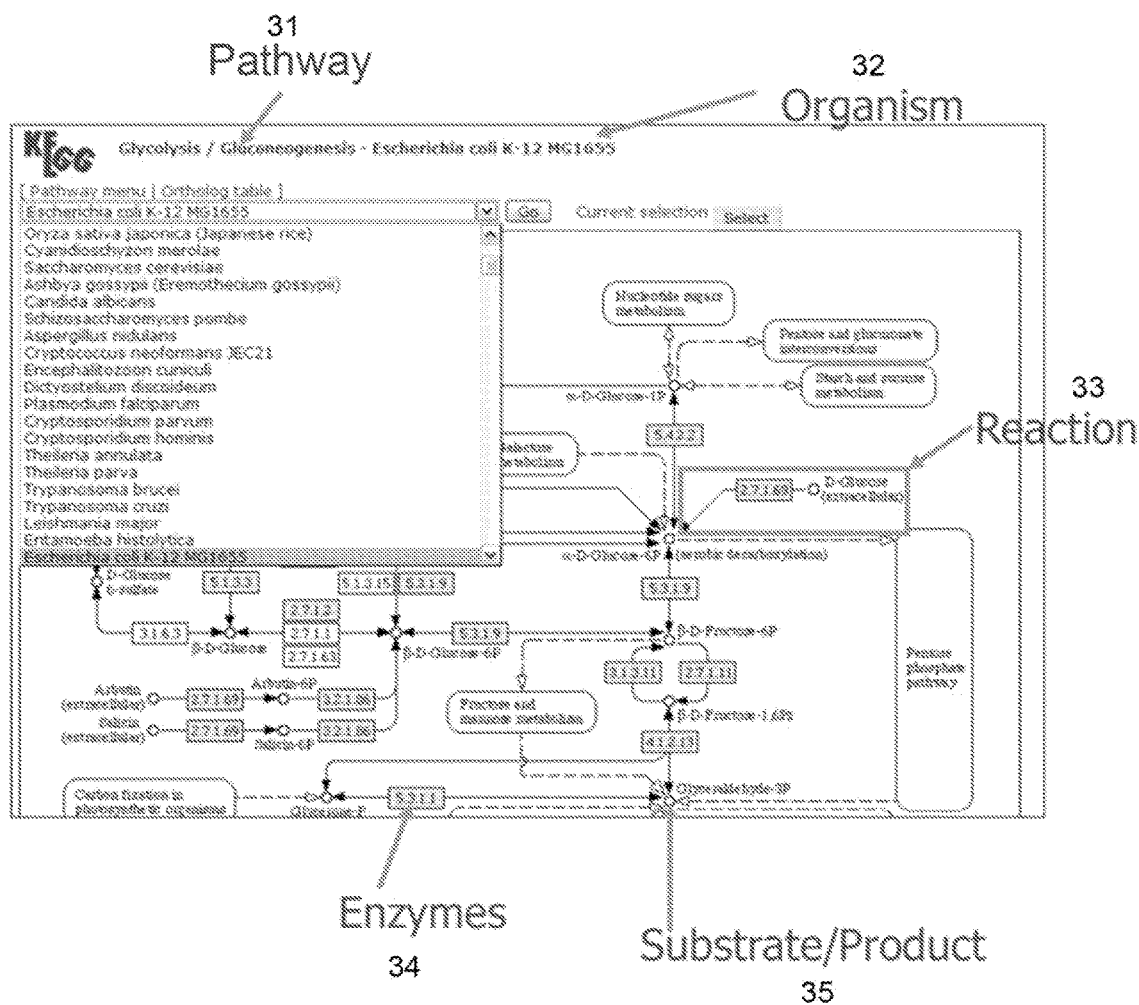
FIG. 5 shows an example of metabolic pathway analysis for a microorganism using the computer-assisted strain construction & development engineering (CASCADE), in accordance with an embodiment of the invention.

FIG. 5 shows an example of metabolic pathway analysis (500) for a microorganism using the computer-assisted strain construction & development engineering (CASCADE), in accordance with an embodiment of the invention. In this particular example, a pathway (31) (i.e. Glycolysis/Gluconeogenesis) for a microorganism (32) (e.g. *Escherichia coli* K-12 MG 1655) is displayed, and graphical examples of a reaction (33) (e.g. D-Glucose extracellular), an enzyme (34) (e.g. 5.3.1.1), and a substrate/product (35) (e.g. Glyceraldehyde-3P) are also displayed. In a preferred embodiment of the invention, this type of metabolic pathway analysis is part of the knowledge pattern search and analysis for derivation of discovered characteristics, which represents a prediction for a desired metabolic property or a desired biological behavior for at least one microorganism.

FIG. 6 shows an exemplary process diagram (600) of wastewater processing and environmentally-friendly energy generation from biological waste materials, in accordance with an embodiment of the invention. In this particular example, the treatment process of wastewater (202) via anaerobic fermentation (214) using specially-selected methanogenic, hydrogenic, and electrogenic microorganisms (212) for generation of hydrogen (206), electricity (210), and cleaned water (209) is disclosed.

In one embodiment of the invention, wastewater (202) may originate from food process industries, domestic, and animal or meat-packing wastes. Using a single microorganism or a combination of multiple microorganisms (212), hydrogen as a product of renewable energy (206) can be recovered from the anaerobic fermentation process (214) accompanying the wastewater treatment. Furthermore, in this embodiment of the invention, the end products (204) from the fermentation process (214), such as acetic acid (acetate), butyric acids (butyrate), propionic acid, ethanol, and/or lactate, can be fed into a Microbial Fuel Cell (MFC) (208) to generate electricity as a product of renewable energy (210). At the same time, the remainder of the wastewater can be further treated to be cleaned water (209), using the same or different microorganisms (212). The knowledge pattern search and analysis method (e.g. CASCADE) for selecting microorganisms based on a desired metabolic property or a desired biological behavior can be utilized for identification and selection of the methanogenic, hydrogenic, and electrogenic microorganisms (212) in this embodiment of the invention.

Figure 7:
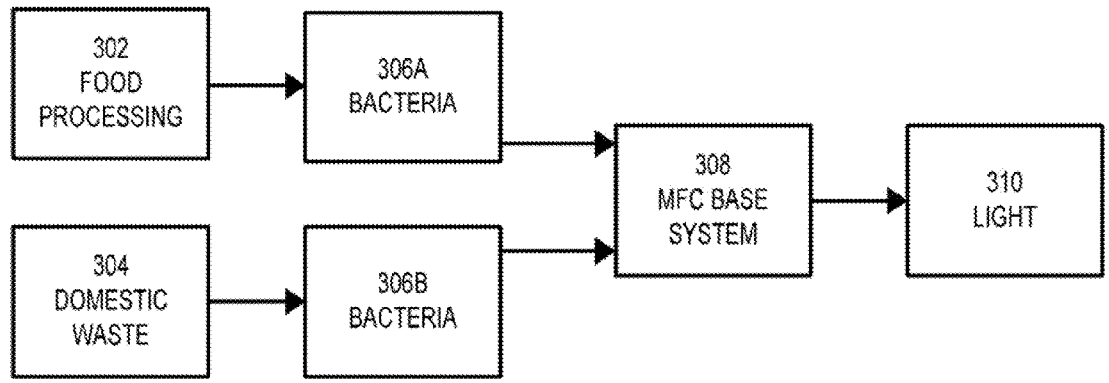
FIG. 7 shows an example of biological waste material processing and environmentally-friendly energy generation from biological waste materials, in accordance with an embodiment of the invention.

FIG. 7 shows an exemplary process diagram (700) for the biological waste material processing and environmentally-friendly energy generation from biological waste materials, in accordance with an embodiment of the invention. In this particular example, food processing waste (302) receives a first set of specially-selected bacteria (306A) based on the knowledge pattern search and analysis method (e.g. CASCADE) for selecting microorganisms. Domestic waste (304) receives a separate, second set of specially-selected bacteria (306B) based on the knowledge pattern search and analysis method (e.g. CASCADE) for selecting microorganisms. Then, the output from the biochemical interactions in the two separate sets of specially-selected bacteria (306A, 306B) with the two separate types of biological waste materials (302, 304) is fed into an MFC-based electricity generation system (308), which is operatively connected to an electrical appliance such as a light bulb (310).

Figure 8:
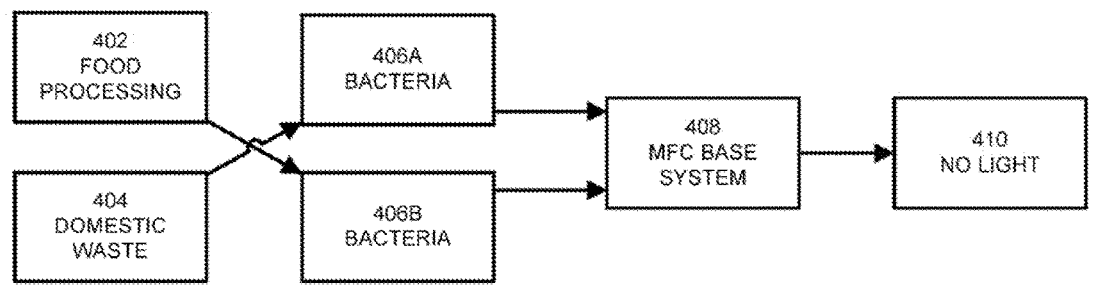
FIG. 8 shows an example of biological waste material processing and inefficient energy generation from biological waste materials due to a wrong selection of microorganisms.

FIG. 8 shows an example (800) of biological waste material processing and inefficient energy generation from biological waste materials due to a wrong selection of microorganisms. In this ineffective case of renewable energy generation, a first set of bacteria (406A), which is optimized for food processing waste (402), is accidentally used for domestic waste (404), while a second set of bacteria (406B), which is optimized for the domestic waste (404), is accidentally used for the food processing waste (402). Because purpose-specific microorganisms (406A, 406B) for specific waste materials (402, 204) are accidentally switched, the resulting output from an MFC-based electricity generation system (408) produces inefficient amount of electricity or no electricity (i.e. 410).

Two examples as illustrated and described for FIG. 7 and FIG. 8 show that selecting and optimizing purpose-specific microorganisms are important for efficient generation of renewable energy from biological waste materials, because the efficiency of the renewable energy output is sensitive to the selection of microorganisms with desirable metabolic properties or biological behaviors.

Methods and systems for knowledge pattern search and analysis for selecting microorganisms based on desired metabolic properties or biological behaviors can be used in a variety of wastewater or biological waste management applications. For example, the wastewater or biological waste management system in accordance with an embodiment of the present invention can be installed on a ship (e.g. a military ship, a commercial ship) to process wastewater or biological wastes on the ship. Furthermore, this system can also generate hydrogen, electricity, methane, or other forms of renewable energy to be used on the ship.

In another example, the wastewater or biological waste management system in accordance with an embodiment of the present invention can be installed at a sugar plant, a brewery, a winery, a dairy, or beverage plants to process their wastewaters. The wastewaters from these facilities contain higher sugar, grain, carbohydrates, and other organic substances for renewable energy to be extracted using an embodiment of the present invention. In the U.S. alone, there are about 24,000 such factories, which may need wastewater treatments or recycles.

Yet in another example, the wastewater or biological waste management system in accordance with an embodiment of the present invention can be installed on a site of municipal wastewater treatment facilities to clean the water and generate environmentally-friendly energy to cover current expensive aerating process.

Yet in another example, the wastewater or biological waste management system in accordance with an embodiment of the present invention can be installed on a farm for animal waste treatments to generate more effective renewable energy than the current biogas generation process.

Figure 9:
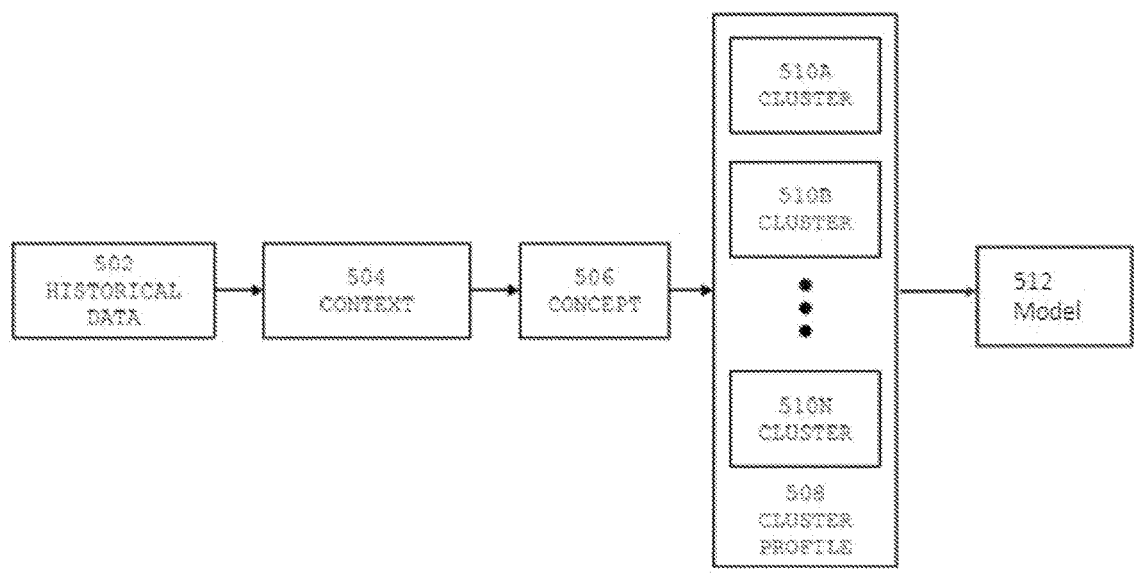
FIG. 9 shows a knowledge pattern discovery process to construct a pattern-identifying model, wherein the knowledge pattern discovery involves contextualization, conceptualization, and clustering of historical data for a computerized data network, in accordance with an embodiment of the invention.

FIG. 9 shows a knowledge pattern discovery process (900) to construct a pattern-identifying model (512), wherein the knowledge pattern discovery involves contextualization (504), conceptualization (506), and clustering (508, 510A-510N) of historical data (502) for a computerized data network, in accordance with an embodiment of the invention. In a preferred embodiment of the invention, the knowledge pattern discovery process is a data processing and analysis procedure configured to be executed on a CPU and a memory unit of one or more learning agents (e.g. computer systems, portable electronic devices, sensor devices, and etc.).

In the preferred embodiment of the invention, the knowledge pattern discovery process as shown in FIG. 9 involves analyzing at least some historical data (502) using a context-concept-cluster (CCC) data analysis method to construct a pattern-identifying model (512), which can then be used for static and dynamically-updated data pattern detection, monitoring, and prediction (e.g. FIG. 10).

As shown in FIG. 9, in the preferred embodiment of the invention, the historical data (502), which may be a collection of textual data, multimedia data, or any other data accumulated by one or more computer systems, is first processed by a contextualization module (504). In one or more embodiments of the invention, "contextualization" of input historical data (e.g. 502) utilizes a user-defined context (e.g. a condition, a keyword, or a desired target information) to identify certain information which contains these contexts. For example, if the user-defined context is finding information regarding highest gene similarity scores, gene usages in metabolic pathways (e.g. enzymes, substrates, and/or products), or percentage of gene usages in certain functional categories in Kyoto Encyclopedia of Genes and Genomes (KEGG) or another library of genetic and/or genome data, then pertinent information may be identified by the contextualization module (504).

Then, for some pieces of information which are not readily identified for certain useful patterns (e.g. as defined by a user) in the contextualization module (504), a conceptualization module (506) can be utilized to group information together based on an EC (element-and-context) matrix and a CC (context-and-concept) matrix. For a preferred embodiment of the invention, the EC matrix is shown as Table 1 and four equations for probability, lift, difference, and correlation calculations. Furthermore, for the preferred embodiment of the invention, the CC matrix is shown as Table 2.

In a preferred embodiment of the invention as shown in FIG. 9, Table 1, and Table 2, the EC matrix and CC matrix calculation approach enables the system for the knowledge pattern search to group unfamiliar (e.g. outside the range of user-defined context) information together with other information, which are determined to be closely associated with this unfamiliar information. In one embodiment of the invention, the conceptualization module (506) may be particularly useful if certain information falls outside of the user-defined context and needs to be grouped with other elements and contexts. For example, if the user-defined context is finding information regarding highest gene similarity scores, gene usages in metabolic pathways (e.g. enzymes, substrates, and/or products), or percentage of gene usages in certain functional categories in Kyoto Encyclopedia of Genes and Genomes (KEGG) or another library of genetic and/or genome data, then pertinent information may be identified by a system for the knowledge pattern search in accordance with an embodiment of the present invention. This process of finding information based on the user-defined context is called "contextualization."

Continuing with FIG. 9, in a preferred embodiment of the invention, a cluster profile module (508) comprises one or more clusters (i.e. 510A, 510B, . . . , 510N), wherein each cluster stores grouped, categorized, and/or sorted information based on proximity or "closeness" of information discovered or determined by contextualization and conceptualization processes. For example, a list of elements may be produced as an output of contextualization, and a list of concepts may be produced as an output of conceptualization. In this example, if the list of elements and the list of concepts have a close semantic proximity based on a probability calculation, a lift calculation, a difference calculation, a correlation calculation, an EC matrix, a CC matrix, and/or a standard deviation among elements, contexts, and concepts, some of which are shown in Tables 1~5, then this list of elements and the list of concepts may be categorized and stored in the same cluster.

For one or more embodiments of the invention, the methods of defining and relating several aspects of data contents among each other are shown in Tables 1~5. In various embodiments of the invention, elements, contexts, concepts, sequences, and clusters are important aspects of data contents for semantic analysis, which can be defined as mathematical concepts. For example, Table 1 shows an example of an EC matrix (element-and-context relation), which may be quantified with a "probability" calculation, a "lift" calculation, a "difference" calculation, and a "correlation" calculation, in accordance with an embodiment of the invention. In one embodiment of the invention, an EC value may represent a proximity of association between an element (Wk) and a context (n), wherein the EC value may be quantified by one or more of the calculations related to probability, lift, difference, and correlation.

Furthermore, Table 2 shows an example of a CC matrix (context-and-concept relation) in accordance with an embodiment of the invention, wherein a CC value may represent an average EC value of the elements belonging to a concept (m). Therefore, a high CC value may indicate an overall coherence of association between elements and contexts for a particular concept (m), and a low CC value may indicate an overall looseness/incoherence of association between elements and contexts for the particular concept (m).

Moreover, Table 3 shows an example of a SC matrix (concept-and-sequence relation), in accordance with an embodiment of the invention. A high SC value may indicate "closeness" or coherence of a concept (m) to a sequence (t), and a low SC value may indicate "looseness" or incoherence of the concept (m) to the sequence (t). In addition, Table 4 shows an example of a concept-and-cluster relation, in accordance with an embodiment of the invention. A concept-and-cluster relation value represents an average of SC (concept-and-sequence relation) values for a particular cluster (l). Therefore a high concept-and-cluster relation value may indicate a general "closeness" or coherence of concepts and sequences per cluster, while a low concept-and-cluster relation value may indicate a general "looseness" or incoherence of concepts and sequences per cluster. Furthermore, Table 5 shows a context-concept-cluster (CCC) matrix, in accordance with an embodiment of the invention.

FIG. 10 shows an example (1000) of applying a constructed pattern-identifying model (512) to static and dynamically-updated data (602) associated with a computerized data network for data pattern analysis (i.e. by using 606 and 608), calculation of a data profile match score (i.e. 610), and/or a gains analysis (i.e. 612), in accordance with an embodiment of the invention. In one embodiment of the invention, the data profile match score may be computed in an profile match score module (610) based on outputs of the pattern-identifying model (512) and data patterns (i.e. 606, 608). In one embodiment of the invention, a high data profile match score indicates a high likelihood of data anomaly, and a low data profile match score indicates a low likelihood of data anomaly. In a preferred embodiment of the invention, the pattern-identifying model (512) for data sets of interest (e.g. 502 of FIG. 9) is formulated by a knowledge pattern discovery process (900 of FIG. 9), which generally involves a context-concept-cluster (CCC) data analysis method as described for FIG. 9. Furthermore, in one embodiment of the invention, a gains analysis (i.e. 612) can compute a lift value as previously described for the second table (300B) in FIG. 3. The gains analysis (i.e. 612) can also measure another indicator which distinguishes or shows a specific trait in a small population of microorganisms (e.g. the smart bacteria population with a desired behavior like methanogenic properties vs. generic bacteria population).

Once the pattern-identifying model (512) is constructed, this model can be applied to the static and dynamically-updated data (602) to discover and identify similarity patterns (606) and prediction patterns (608). In one or more embodiment of the invention, the similarity patterns (606) can be identified by group and cluster characteristics measured by user-defined context, keywords, and/or the context-concept-cluster (CCC) data analysis method, as shown in FIG. 9 and Tables 1~5. The prediction patterns (608) (e.g. discovered characteristics) can be discovered from the historical data by correlating one or more microorganisms with pathway characteristics, which can be stored in a particular cluster (a cluster in the cluster profile (508)). Then, concept projection (EQ. 1001) and/or Gaussian distance to a cluster (EQ. 1003) may be calculated to derive an profile match score (610).

In a preferred embodiment of the invention, the profile match score (610) derived from static and dynamically-updated information favors a smaller cluster because the profile match score (610) can be calculated as the Gaussian distance divided by the size of a cluster, which is associated with the number of sequences in the cluster. Information in a smaller cluster may also suggest, though not necessarily so, relatively unique information contained in the cluster. Furthermore, a gains analysis (612) may be performed to sort the static and dynamically-updated data (602) according to the derived profile match score (610). The gains analysis (612) may indicate usefulness or worthiness of a particular set of the static and dynamically-updated data (602).

Figure 11:
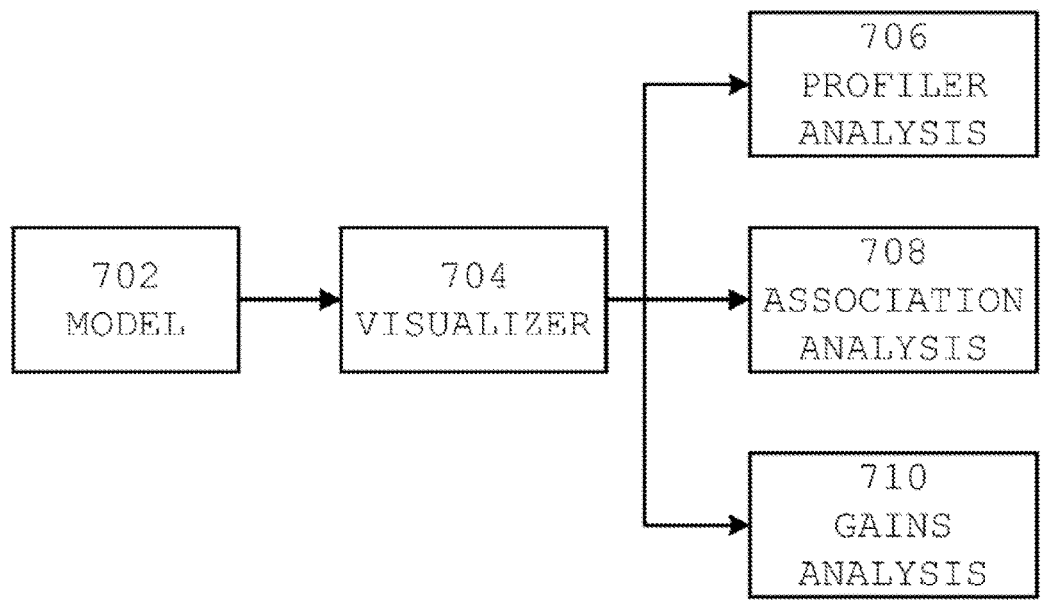
FIG. 11 shows a plurality of components in a knowledge visualization module associated with a computerized data network, in accordance with an embodiment of the invention.

FIG. 11 shows a plurality of components (1100) in a knowledge visualization module (704) associated with a computerized data network, in accordance with an embodiment of the invention. In a preferred embodiment of the invention, outputs from a pattern-identifying model (702) can be fed into the knowledge visualization module (704), which may assist displaying of information related to data or analytical information, such as information from a profiler analysis module (706), an association analysis module (708), and a gains analysis module (710). In the preferred embodiment of the invention, the knowledge visualization module (704) is configured to send visualization data to a graphics chip in a computer system or another component in a system for knowledge pattern search, so that the graphics chip can transmit display information to a computer monitor or another visual display.

Figure 12:
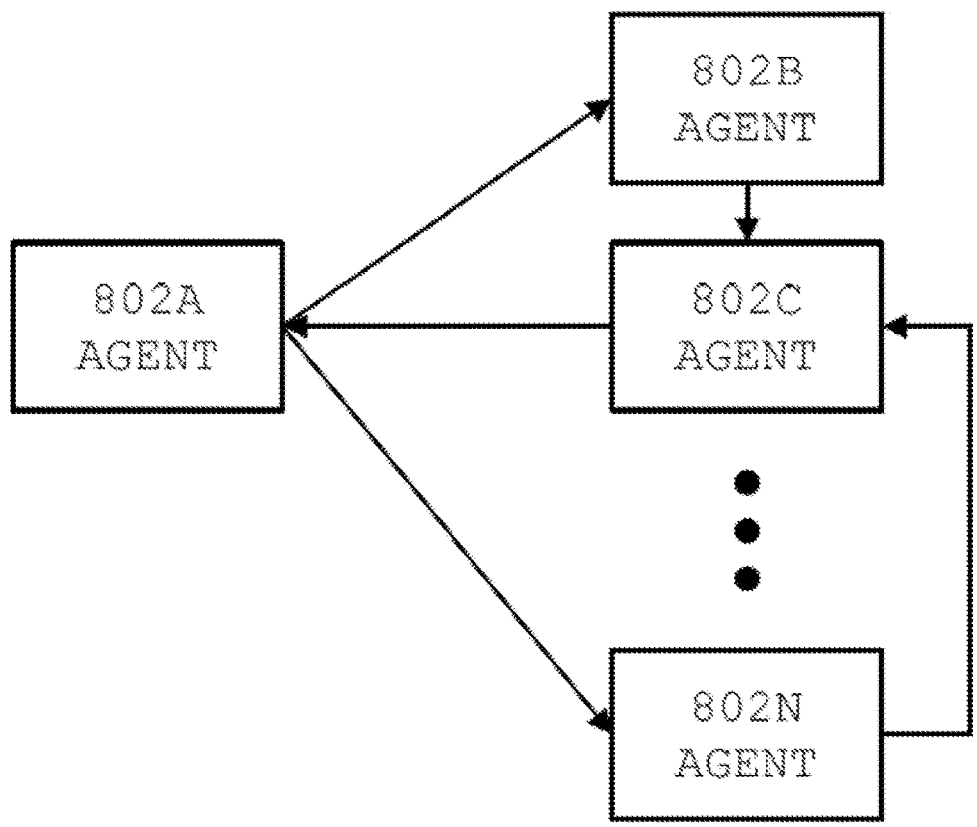
FIG. 12 shows a general collaborate search concept involving a multiple number of learning agents associated with a computerized data network, in accordance with an embodiment of the invention.

FIG. 12 shows a general collaborative search concept (1200) involving a multiple number of learning agents (802A, 802B, 802C, . . . , 802N) associated with a computerized data network, in accordance with an embodiment of the invention. In a preferred embodiment of the invention, each learning agent may be a computer system, a portable electronics device, a sensor system, or another system capable of processing computerized data with a CPU, a memory unit, and/or a data storage unit.

Furthermore, in the preferred embodiment of the invention, each learning agent may contain its own pattern-identifying model based on its own knowledge pattern discovery process (e.g. FIG. 9) and clustering of contextualized and conceptualized historical data. Yet in another embodiment of the invention, the plurality of learning agents may share a single pattern-identifying model or share a multiple number of pattern-identifying models, so that each learning agent does not necessarily have to process its own knowledge pattern discovery process, including contextualization, conceptualization, and clustering of historical data for every learning agent.

A plurality of these learning agents may be operatively connected together via data networks to work collaboratively as a distributed system or a cooperative system. The multiple learning agent configuration as shown in FIG. 12 may reduce the burden of data processing, transmission, and analysis time by utilizing a distributed system or a cooperative system which comprises a multiple number of learning agents, compared to a centralized architecture in which all relevant data is transmitted to a particular system for data processing and analysis.

Figure 13:
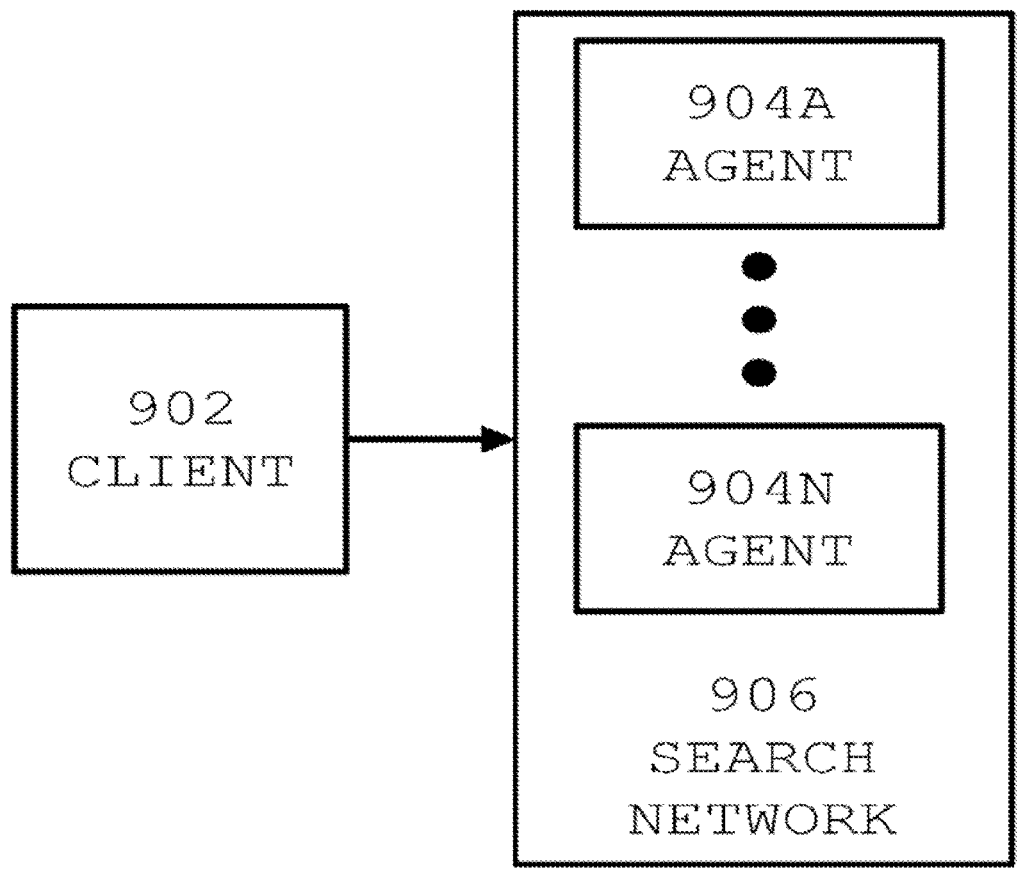
FIG. 13 shows a diagram showing a collaborative search return results from a computerized data network with the multiple number of learning agents, in accordance with an embodiment of the invention.

FIG. 13 shows a diagram (1300) showing a collaborative search return results from a multiple number of learning agents (904A, . . . , 904N) comprising a search network (906), in accordance with an embodiment of the invention. As shown in FIG. 13, a user or a client (902) is able to access search results provided by the search network (906), which comprises a multiple number of learning agents (904A, . . . , 904N).

Figure 14:
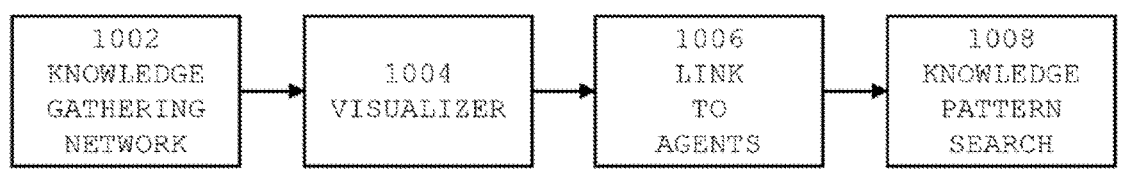
FIG. 14 shows an interaction diagram among different modules in a collaborative search return environment involving a multiple number of learning agents, in accordance with an embodiment of the invention.

FIG. 14 shows an interaction diagram (1400) among different modules in a collaborative search return environment involving a multiple number of learning agents, in accordance with an embodiment of the invention. In one embodiment of the invention, a knowledge-gathering network (1002) is operatively connected to a visualization module (1004). This visualization module (1004) may be operatively connected to a plurality of learning agents (1006), which are capable of performing a knowledge pattern search and analysis (1008).

To demonstrate a practical example of using the context-concept-cluster (CCC) data analysis method as shown in FIG. 9 to construct a pattern-identifying model (512), and also to demonstrate an application of this pattern-identifying model (512) to static and dynamically-updated data (602) for pattern identification and analysis as shown in FIG. 10, an example using Kyoto Encyclopedia of Genes and Genomes (KEGG) and/or another library of genes and genome data as historical data (e.g. 502 of FIG. 9) and static and dynamically-updated data (602 of FIG. 10) is described below:

In this particular example, new, unique, and information of interest refers to new piece of genetic, genome, or other biochemical information relevant to one or more microorganisms.

1. Historical Data (502 of FIG. 9)

Kyoto Encyclopedia of Genes and Genomes (KEGG) and/or another library of genes and genome data are assumed to be used in this example, wherein the data are publicly available as follows:

a) Structured data: standardized information associated with genetic and chemical fingerprints of metabolic and energy-generating biological enzymes, substrates, and/or products from Kyoto Encyclopedia of Genes and Genomes (KEGG) and/or another library of genes and genome data b) Unstructured data: unstructured textual information or other data associated with certain microorganisms and pathways (e.g. enzymes, substrates, and/or products)

c) Newly-updated information: Library/database of genes and genome data which merely older than a few minutes of real-time data stream.

In this example, the data are periodically mined and separated into patterns and data anomalies, hence enabling an early detection of changing characteristics of biochemical materials, microorganisms, and/or genetic information. For example, the Kyoto Encyclopedia of Genes and Genomes (KEGG) and/or another library of genes and genome data which are updated weekly or in another time duration can be categorized into n characteristics groups using the context-concept-cluster algorithm (CCC) shown in FIG. 9.

In this example, the CCC algorithm is used to parse the historical data (e.g. gene and genome information for microorganisms). The steps of the CCC algorithm are described below in three steps. For this example, each sentence, paragraph, or article can be set as a "sequence," and a word in a sentence is set as an "element" for the following process below:

Step 1 (e.g. 504 of FIG. 9):

Assuming a sequence t with $W_k$ (k=1, 2, . . . , K), this example selects a set of Context n (n=1, 2, . . . , K), which is a subset of the elements in t, where their occurrences are larger than other elements outside the context set. Then, as shown in Table 1 in the drawings, a system executing the knowledge pattern discovery process (e.g. 900 of FIG. 9, wherein the system may be a computer system, a portable electronic device, a sensor device, a learning agent, and etc.) can compute the association between each "element," $W_k$, with "Context," n.

This example uses four methods of computing the element-and-context relation (EC) as follows:

$$\text{Probability: } P(W_k \mid n) = \frac{\text{\# of instances when } W_k \text{ follows (or precedes)} n}{\text{\# of instances of } n}$$

$$\text{Lift: } L(W_k, n) = \frac{p(w_k \mid n)}{p(w_k)}$$

$$\text{Difference: } D(W_k, n) = P(W_k \mid n) - P(W_k)$$

$$\text{Correlation: } R(W_k, n) = \frac{\sum_{t=1}^{T} (\# \ w_k \text{ in } t) * (\# \text{ of } n \text{ in } t)}{\sqrt{\sum_{t=1}^{T} (\# \ w_k \text{ in } t)^2} * \sqrt{\sum_{t=1}^{T} (\# \text{ of } n \text{ in } t)^2}}$$

where t represents a sequence, such as a sentence; $W_k$ stands for an element, such as a word in a sentence; n stands for context, such as an element next to $W_k$.

Step 2 (e.g. 506 of FIG. 9):

Continuing with the example followed from Step 1, "concepts" are generated and labeled as Concept, m, (m=1, 2, . . . , M) by clustering all elements $W_k$ based on the EC matrix in Table 1. For each cluster, the system executing the knowledge pattern discovery process (e.g. 900 of FIG. 9) can compute the average association between an element and a context as a context-and-concept relation denoted as CC in Table 2.

Step 3 (e.g. 508 of FIG. 9):

Continuing with the example followed from Step 1 and Step 2 above, the system executing the knowledge pattern discovery process (e.g. 900 of FIG. 9) can project the original sequence of elements into concepts by summing all context-and-concept (CC) relations over the number of contexts in a sequence, t, as shown in Table 3.

After this process, each sequence can be represented as a numeric association with a set of concepts, m=1, 2, . . . , M. In this example, the SC matrix shown in Table 3 may be used for clustering sequences.

The clustering of contextualized and conceptualized Kyoto Encyclopedia of Genes and Genomes (KEGG) and/or another library of genes and genome data contains a list of average concept-and-sequence relation values per cluster, as shown in Table 4. After the clustering of data is complete (e.g. 510A, 510B, . . . , 510N in 508 of FIG. 9), the data processed through this context-concept-cluster (CCC) data analysis method can be placed as key-value lookup table pairs, as shown in Table 5. This key-value lookup table pairs, as shown in Table 5, may be called a CCC pattern-identifying model (e.g. 512 of FIG. 9 and FIG. 10). It may be desirable to place relational calculations associated with contexts, concepts, and clusters as lookup table values, and keywords derived from contexts and concepts as lookup table keys, as shown in Table 5.

2. New and Dynamically-Updated Data (e.g. 602 of FIG. 10)

Continuing with the example of processing of historical data described above, the CCC pattern-identifying model (e.g. 512 of FIG. 9) constructed through the context-concept-cluster (CCC) data analysis method is now ready to be applied to new and dynamically-updated data (e.g. 602 of FIG. 10) to determine and identify various patterns worthy of analysis.

In this example, static and dynamically-updated data can be Kyoto Encyclopedia of Genes and Genomes (KEGG) and/or another library of genes and genome data within certain period of real time (e.g. weekly), and they are evaluated for similarity patterns (606) and prediction patterns (608) for gene similarities, gene usages in metabolic pathways, percentages of genes in certain functional categories, codon usages, and distribution of gene usages in certain metabolic function categories. Each characteristic group or cluster (e.g. 510A, 510B, . . . , 510N in 508 of FIG. 9) described using the keywords (e.g. contexts, concepts and clusters in Table 5) associated with values is essentially a similarity pattern. On the other hand, a prediction pattern is discovered from the historical data by linking or correlating discovered characteristics, such as a prediction for a desired metabolic property or a desired biological behavior, with the keywords describing one or more clusters containing key-value lookup table pairs in the CCC pattern-identifying model (e.g. 512 of FIG. 9 and FIG. 10), which is constructed from the historical data (e.g. 502 of FIG. 9). Examples of keywords discovered from the CCC pattern-identifying model may be the pathway characteristics previously described for the second table (300B) in FIG. 3. Once these keywords or characteristics are discovered from the CCC pattern-identifying models, the discovered keywords or characteristics can be used directly to screen new or dynamically-updated data.

In this example, each piece of new information (i.e. new and dynamically-updated data (602) or a new sequence τ below) may be decomposed into contexts, concepts and clusters and analyzed in the pattern-identifying model (512), which identifies similarity patterns (606) and prediction patterns (608). Then, an profile match score (610) may be quantified by applying a CCC model on a new sequence, τ, as shown below:

Score for a new sequence, τ=Gaussian distance of concept projection of τ to Cluster l, where $$\text{Concept Projection of } \tau = \frac{\sum \text{All } CC \text{ in } \tau}{\sqrt{\# \text{ of unique context in } \tau}} \quad 1.$$

Gaussian distance to Cluster $l =$    2.

$$\frac{e^{-\frac{1}{2}\|\text{Concept Projection of } \tau(m\times 1) - \text{Average } SC(m,l)\|}}{\sum_l e^{-\frac{1}{2}\|\text{Concept Projection of } \tau(m\times 1) - \text{Average } SC(m,l)\|}}$$

In this particular example, the Gaussian distance represents the likelihood of the new sequence τ belonging to Cluster l. The profile match score (610) is the Gaussian distance divided by the size (e.g. number of sequences or sentences) in Cluster l, which may predict a usefulness of one or more microorganisms with one or more discovered characteristics for generating environmentally-friendly energy from biological waste materials.

Following this Kyoto Encyclopedia of Genes and Genomes (KEGG) and/or another library of genes and genome data example, in the gains analysis (612), the static and dynamically-updated data is sorted according to the profile match score. The real-life gains or measures for value, or "worthiness" of the Kyoto Encyclopedia of Genes and Genomes (KEGG) and/or another library of genes and genome data can be computed along the sorted list.

For example, critical pathways and/or pathway characteristics derived from Kyoto Encyclopedia of Genes and Genomes (KEGG) and/or another library of genes and genome data clusters may be considered more worthy, because these critical pathways and/or pathway characteristics for a desired metabolic property or biological behavior may be instrumental in boosting efficiency of certain metabolic properties or biological behaviors for environmentally-friendly energy generation. In this case, these critical pathways and/or pathway characteristics may belong to one or more clusters characterized by a higher level of usefulness. The sizes of clusters containing the critical pathways and/or pathway characteristics may be relatively small.

As shown by this example, by analyzing historical data (502) to construct a CCC pattern-identifying model (e.g. 512), a user may notice that there are clusters of information which are not immediately understood for their consequences to metabolic properties or biological behaviors. However, by processing this piece of information from Kyoto Encyclopedia of Genes and Genomes (KEGG) and/or another library of genes and genome data through the constructed CCC pattern-identifying model (e.g. 512) to identify similarity patterns (606) and prediction patterns (608) as shown in FIG. 10, the user may be able to understand that certain metabolic and energy-generating biological pathways and pathway characteristics may link more to desirable metabolic properties and biological behaviors than others for certain microorganisms.

The correlation is between certain energy-generating biological pathways and pathway characteristics and desirable metabolic properties and biological behaviors for certain microorganisms can be presented as a pattern identified from the historical data during the construction of the CCC pattern-identifying model (e.g. 512). It is feasible that in real-life situations of using the system for knowledge pattern search and analysis, the value of certain prediction patterns may change over time. In some situations, it may be important to periodically update the CCC pattern-identifying model (e.g. 512) with new pattern correlations (i.e. updates to Table 5) to make its semantic analysis more accurate to ever-changing dynamic information contents and data flow in computerized data networks which may store Kyoto Encyclopedia of Genes and Genomes (KEGG) and/or another library of genes and genome data.

3. Multiple Learning Agent System (e.g. FIG. 12)

Continuing with Kyoto Encyclopedia of Genes and Genomes (KEGG) and/or another library of genes and genome data example above, several genetic and genome libraries and databases can be monitored in real-time or periodically by utilizing multiple learning agents (e.g. 802A, 802B, 802C, . . . , 802N of FIG. 12). The multiple learning agents can also be installed in multiple computer systems operatively connected to each other. In a preferred embodiment of the invention, the pattern-identifying models in each learning agent are updated periodically (e.g. weekly) and are stored locally in each learning agents' data storage and/or indexes.

The multiple number of learning agents can make a collaborative decision and perform gains analysis to predict desired metabolic properties and/or biological behaviors of certain microorganisms. The gains analysis may also help determining the significance/relevance of a new piece of information in the Kyoto Encyclopedia of Genes and Genomes (KEGG) and/or another library of genes and genome data. The significance/relevance can be evaluated against both similarity and prediction patterns in one or more CCC pattern-identifying models (e.g. 512) in the multiple number of learning agents working collaboratively as a distributed system or a cooperative network system.

Furthermore, in another example of implementing an embodiment of the present invention, the system for knowledge pattern search for multiple network learning agents comprises four parts, as shown below:

Part 1: Knowledge Gathering Network

In this example, Part 1 is a knowledge-gathering network which presents a total view of information, knowledge, and objects that are engaged in a knowledge management process. For this example, the knowledge-gathering network is an XML-based knowledge gathering, creation, and dissemination system that mines, learns, and discovers knowledge patterns from historical data. The knowledge patterns are stored as a pattern-identifying model locally in a learning agent. In this particular example, the knowledge gathering network contains the following components:

Component 1: Gathers historical data via a data-gathering module. At a high level, this component defines how genetic, genome, and biochemical data is organized and flows into a knowledge management process. An XML data schema or ontology describes how concepts are hierarchically organized in the process to store them into an XML Warehouse.

Component 2: Imports data into an XML Warehouse. ETL (i.e. extract, transform, an load) tools in the import engine include adapters for extracting data from a database, word document, Excel, HTML, PDF or PPT source. Furthermore, in this example, transformation tools in the transformation engine built from XSLT are used for loading data into an XML warehouse according to the schema.

Component 3: This component utilizes the CCC analysis model as shown in FIG. 9 to discover knowledge patterns for construction of a pattern-identifying model. Furthermore, in this example, this component discovers correlations and patterns in the XML warehouse using the context-concept-cluster (CCC) data analysis method. The XML warehouse contains raw observations or inputs for a collection of hierarchical objects as for data mining. Data mining can be applied to the objects at any level of the hierarchy. Their input observations can be text, numeric data, or any form of symbolic languages used to describe characteristics of an object or an element. For numeric data, transformations are used to change the numeric data into symbols.

In this example, the context-concept-cluster (CCC) data analysis method is used for information mining. A context (504 of FIG. 9) is a symbol which occurs frequently in a symbolic system. A concept (506 of FIG. 9) is a group of symbols that either appear frequently together or appear frequently together with a same context. Therefore, they are connected by meaning. For this example, an object cluster (510 of FIG. 9) is a characteristic group of objects grouped according to the concepts. The contexts and concepts are discovered automatically. The object cluster profile (508 of FIG. 9) is the foundation of knowledge patterns (512, 606, 608 of FIG. 10).

These knowledge patterns include, for example, similarity patterns and prediction patterns. A similarity pattern (606 of FIG. 10) refers to a group of concepts that are used to describe how objects are similar to each other. A prediction pattern (608 of FIG. 10) establishes a predictive relationship between an earlier analysis of a concept and an actual result observed subsequently to predict likelihood of future events, if an associated concept analyzed earlier occurs.

Component 4: This component utilizes application of a constructed pattern-identifying model (512 of FIG. 9, 512 of FIG. 10) to static and dynamically-updated data (602 of FIG. 10) for analyzing knowledge patterns from the static and dynamically-updated data. For this example, knowledge patterns can be viewed as normal behaviors of the participants in a knowledge management process. They are used to contrast, detect, and predict unusual behaviors, anomalies, or new opportunities that might come to the data network dynamically. The pattern-identifying model (512 of FIG. 9, 512 of FIG. 10) is used to monitor and understand dynamically-updated genetic and/or genome libraries and databases (e.g. Kyoto Encyclopedia of Genes and Genomes (KEGG) and/or another library of genes and genome data). They can also be used to monitor the significance of newly-updated information to desired metabolic properties and/or biological behaviors of microorganisms which are used in environmentally-friendly generation of energy from biological waste materials.

Part 2: Knowledge Pattern Visualization

For this example, a single pattern-identifying model (702 of FIG. 11) from a single agent can be viewed using a visualizer module (704 of FIG. 11). Patterns can be displayed in clusters and concepts, which are sorted according to a chosen metric in a profiler analysis module (706 of FIG. 11). Similarity patterns can be viewed in the profiler analysis module (706 of FIG. 11) and the association analysis module (708 of FIG. 11). The prediction patterns can be viewed in the gains analysis module (710 of FIG. 11).

Part 3: Knowledge Pattern Link

For this example, each learning agent (802A, 802B, 802C, . . . , 802N of FIG. 12) mines, learns, and discovers its own knowledge patterns using its own domain-specific data sets. Then, the learning agent can link to the other learning agents to form a distributed or collaborative search network. For this example, the distributed or collaborative search network may be achieved by implementing a peer-to-peer architecture, and listing other learning agents in each learning agent's peer list.

Part 4: Collaborative Knowledge Pattern Search

For this example, a web client (902 of FIG. 13) can search and find information from a search network (906 of FIG. 13) formed by the learning agents (904A, . . . , 904N of FIG. 13) in the distributed or collaborative search network (906 of FIG. 13). The ranking of search results may be determined by a search content's uniqueness relative to a search context.

Various embodiments of the present invention may provide several advantages over conventional method of wastewater or biological waste material treatments. For example, one or more methods and systems for knowledge pattern search and analysis for selecting microorganisms for purpose-specific requirements (i.e. generating hydrogen, electricity, methane, and etc.) based on desired metabolic properties or biological behaviors can significantly improve efficiency of renewable energy generation from biological waste materials or wastewater.

Furthermore, by providing a computer-implemented method and a computerized system for knowledge pattern search and analysis for selecting microorganisms based on desired metabolic properties or biological behaviors, various embodiments of the present invention can significantly shorten discovery and selection efforts for finding or developing a suitable microorganism for a particular application.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for producing methane, hydrogen, or electricity with optimally-selected microorganisms to generate renewable energy from biological waste materials in a microbial fuel cell (MFC), in a wastewater treatment system, or in another energy-generating reactor, the method comprising the steps of:
   prior to performing a computerized data analysis, designing user-defined and user-desired metabolic smart properties criteria from microorganisms, wherein the user-defined and user-desired metabolic smart properties criteria represent each microorganism's ability to generate at least one of methane, hydrogen, and electricity induced by an anaerobic fermentation that accommodates biochemical interactions or digestion of the biological waste materials by at least a subset of the microorganisms;
   inputting the user-defined and user-desired metabolic smart properties criteria into a machine-learning processing system;
   generating combinations and sub-combinations of microorganisms' profiles for methanogenic, hydrogenic, and electrogenic properties designed by the user-defined and user-desired metabolic smart properties criteria in the machine-learning processing system, wherein the combinations and the sub-combinations of microorganisms' profiles contain genetic and chemical fingerprints of metabolic and energy-generating biological pathways specific to the user-defined and user-desired metabolic smart properties criteria;
   grouping the microorganisms into pathway characteristics by utilizing the combinations and sub-combinations of the microorganisms' profiles designed by the user-defined and user-desired metabolic smart properties criteria, wherein the step of grouping is executed on a CPU and a memory unit of the machine-learning processing system;
   identifying a newly-discovered microorganism from the machine-learning processing system from the pathway characteristics;
   generating a scoring system from the machine-learning processing system to quantify each microorganism's ability to satisfy the methanogenic, the hydrogenic, and the electrogenic properties designed by the user-defined and user-desired metabolic smart properties criteria;
   executing the scoring system in the machine-learning processing system to quantify whether the newly-discovered microorganism from the machine-learning processing system has a higher or lower likelihood of satisfying the user-defined and user-desired metabolic smart properties criteria; and
   generating methane, hydrogen, or electricity with the newly-discovered microorganism in the wastewater treatment system, in the microbial fuel cell (MFC), or in another energy-generating reactor, if the newly-discovered microorganism has the higher likelihood of satisfying the user-defined and user-desired metabolic smart properties criteria.

2. The method of claim 1, wherein the anaerobic fermentation results in at least one of acetic acid, butyric acid, propionic acid, ethanol, and lactate, which generate electricity in the microbial fuel cell (MFC).

3. The method of claim 1, wherein the genetic and chemical fingerprints of metabolic and energy-generating biological pathways include a number of substrates consumed and products produced in reactions as a result of the anaerobic fermentation and generation of electricity in the microbial fuel cell (MFC).

4. The method of claim 1, wherein the pathway characteristics are a collection of biochemical reactions involving one or more of enzymes, substrates, and/or products.

5. The method of claim 1, wherein each pathway among the metabolic and energy-generating biological pathways is at least one biochemical step or link, with a start and an end.

6. The method of claim 1, wherein the machine-learning processing system incorporates concept projection calculation and/or a Gaussian distance to cluster calculation for generating profile match scores from the scoring system.

7. The method of claim 1, wherein the microorganisms comprise natural or genetically-engineered bacteria, fungi, archaea, protists, or a combination thereof.

8. The method of claim 1, wherein the biological waste materials comprise at least one of food and drink processing wastewaters, domestic wastewaters, animal or meat-packing wastes, metal wastes, nuclear wastes, and byproducts of industrial processes.

9. The method of claim 1, wherein the metabolic and energy-generating biological pathways comprise metabolism pathways, genetic information processing pathways, environmental information processing pathways, and cellular processes pathways.

10. The method of claim 1, wherein the genetic and chemical fingerprints of the metabolic and energy-generating biological pathways comprise gene similarity scores along a metabolism pathway among microorganisms, gene usages in the metabolism pathway, a percentage of gene usages for a particular function category, codon usages, and a distribution of gene usages for the particular function category.

11. The method of claim 1, wherein the user-defined and user-desired metabolic smart properties criteria include an ability to utilize or digest certain substrates, an ability to undergo aerobic respiration or anaerobic fermentation, or an ability to produce methane, hydrogen, electricity, or another desired product.

12. The method of claim 1, wherein the one or more microorganisms' profiles in the computer database system are texts or other relevant data describing a plurality of microorganisms including genomic information, codon usages, gene distributions along the metabolic and energy-generating biological pathways, gene distributions for a particular functional category, gene similarity among the one or more microorganisms, and/or generic functions of genes.

13. The method of claim 1, wherein the pathway characteristics are an average or unique number of genes in a metabolism pathway, a gene function category, or an average codon usage frequency relative to the metabolic and energy-generating biological pathways.

* * * * *